US010519247B2

(12) United States Patent
Ward et al.

(10) Patent No.: US 10,519,247 B2
(45) Date of Patent: Dec. 31, 2019

(54) TARGETING HER2 AND HER3 WITH BISPECIFIC ANTIBODIES IN CANCEROUS CELLS

(71) Applicant: Board of Regents, The University of Texas System, Austin, TX (US)

(72) Inventors: E. Sally Ward, Dallas, TX (US); Raimund Ober, Dallas, TX (US); Jeffrey Kang, Dallas, TX (US); Jayakumar Poovassery, Dallas, TX (US)

(73) Assignee: Board of Regents,The University of Texas System, Austin, TX (US)

( * ) Notice: Subject to any disclaimer, the term of this patent is extended or adjusted under 35 U.S.C. 154(b) by 0 days.

(21) Appl. No.: 15/023,648

(22) PCT Filed: Oct. 31, 2014

(86) PCT No.: PCT/US2014/063559
§ 371 (c)(1),
(2) Date: Mar. 21, 2016

(87) PCT Pub. No.: WO2015/066543
PCT Pub. Date: May 7, 2015

(65) Prior Publication Data
US 2016/0229920 A1 Aug. 11, 2016

Related U.S. Application Data

(60) Provisional application No. 61/899,032, filed on Nov. 1, 2013.

(51) Int. Cl.
C07K 16/32 (2006.01)
A61K 39/395 (2006.01)
C07K 16/28 (2006.01)
A61K 45/06 (2006.01)
A61K 31/517 (2006.01)
A61K 39/00 (2006.01)

(52) U.S. Cl.
CPC ............ *C07K 16/32* (2013.01); *A61K 31/517* (2013.01); *A61K 39/39558* (2013.01); *A61K 45/06* (2013.01); *C07K 16/2863* (2013.01); *A61K 2039/505* (2013.01); *C07K 2317/21* (2013.01); *C07K 2317/24* (2013.01); *C07K 2317/31* (2013.01); *C07K 2317/35* (2013.01); *C07K 2317/526* (2013.01); *C07K 2317/56* (2013.01); *C07K 2317/622* (2013.01); *C07K 2317/64* (2013.01); *C07K 2317/73* (2013.01); *C07K 2317/74* (2013.01); *C07K 2317/76* (2013.01); *C07K 2317/77* (2013.01); *C07K 2319/00* (2013.01)

(58) Field of Classification Search
CPC .......................... C07K 16/468; C07K 2317/31
See application file for complete search history.

(56) References Cited

U.S. PATENT DOCUMENTS

| | | | | |
|---|---|---|---|---|
| 5,821,337 A | * | 10/1998 | Carter | C07K 16/28 530/387.3 |
| 2004/0197332 A1 | * | 10/2004 | Ullrich | C07K 16/32 424/145.1 |
| 2008/0108135 A1 | * | 5/2008 | Marks | C07K 16/2881 435/375 |
| 2008/0124345 A1 | * | 5/2008 | Rothe | C07K 16/2863 424/174.1 |
| 2010/0158926 A1 | * | 6/2010 | Cartilage | C07K 16/32 424/174.1 |
| 2010/0256339 A1 | | 10/2010 | Bossenmaier et al. | |
| 2010/0266584 A1 | * | 10/2010 | Schoeberl | A61K 31/337 424/133.1 |
| 2010/0310557 A1 | * | 12/2010 | Keyt | C07K 16/22 424/133.1 |
| 2011/0171222 A1 | * | 7/2011 | Bossenmaier | C07K 16/32 424/138.1 |
| 2011/0256056 A1 | * | 10/2011 | Alper | C07K 16/32 424/1.49 |
| 2012/0107306 A1 | * | 5/2012 | Elis | A61K 39/39558 424/133.1 |
| 2012/0195831 A1 | * | 8/2012 | Zhang | C07K 16/32 424/1.49 |

FOREIGN PATENT DOCUMENTS

| | | | |
|---|---|---|---|
| WO | WO 2001/077342 A1 | 10/2001 | |
| WO | WO 2012/125864 A2 | 9/2012 | |
| WO | WO-2012143523 A1 * | 10/2012 | ......... C07K 16/1063 |
| WO | WO 2013/101993 A3 | 7/2013 | |

OTHER PUBLICATIONS

Xu et al., mAbs 2013; 5:237-254.*
Rudikoff et al., Proc. Nat'l Acad. Sci. USA 79:1979-83 (Year: 1982).*
Brown et al., J. Immunol. 156(9):3285-91 (Year: 1996).*
Bostrom et al., Science 323:1610-14 (Year: 2010).*
Junutula et al., Clin Cancer Res 16:4769-78 (Year: 2010).*
Baeuerle et al., "Bispecific T-cell engaging antibodies for cancer therapy," *Cancer Res*, 69:4941-4944, 2009.
Carter et al., "Humanization of an anti-p185HER2 antibody for human cancer therapy," *Proc Natl Acad Sci U S A*, 89:4285-4289, 1992.
Coloma et al., "Design and production of novel tetravalent bispecific antibodies," *Nat Biotechnol*, 15:159-163, 1997.
Fitzgerald et al., "Rational engineering of antibody therapeutics targeting multiple oncogene pathways," *MAbs*, 3:299-309, 2011.

(Continued)

*Primary Examiner* — Jessica H Roark
(74) *Attorney, Agent, or Firm* — Dentons US LLP

(57) ABSTRACT

The disclosure provides monoclonal bispecific antibodies targeting HER2 and HER3. The disclosure also provides monospecific tetravalent HER3 antigen binding antibodies. Still further provided by the disclosure are methods of treating a cancer in a subject, comprising administering to the subject a therapeutically effective amount of an antibody provided by the disclosure.

12 Claims, 20 Drawing Sheets

Specification includes a Sequence Listing.

(56) References Cited

OTHER PUBLICATIONS

Holbro et al., "The ErbB2/ErbB3 heterodimer functions as an oncogenic unit: ErbB2 requires ErbB3 to drive breast tumor cell proliferation," *Proc Natl Acad Sci U S A*, 100:8933-8938, 2003.

Holliger et al., "'Diabodies': Small bivalent and bispecific antibody fragments," *Proc Natl Acad Sci U S A*, 90:6444-6448, 1993.

Hudson et al., "Engineered antibodies," *Nat Med*, 9:129-134, 2003.

International Search Report for PCT/US2014/063559.

Kang et al., "Engineering multivalent antibodies to target heregulin-induced HER3 signaling in breast cancer cells," *MAbs*, 6:340-353, 2014.

Kol et al., "HER3, serious partner in crime: Therapeutic approaches and potential biomarkers for effect of HER3-targeting," *Pharmacol Ther*, 143:1-11, 2014.

Lee-Hoeflich et al, A central role for HER3 in HER2-amplified breast cancer: Implications for targeted therapy, *Cancer Res*, 68:5878-5887, 2008.

Li et al., "Development of an autocrine neuregulin signaling loop with malignant transformation of human breast epithelial cell," *Cancer Res*, 64:7078-7085, 2004.

"Rapid optimization and prototyping for therapeutic antibody-like molecules," *MAbs*, 5:237-254, 2013, Xu et al.

McDonagh et al., "Antitumor activity of a novel bispecific antibody that targets the ErbB2/ErbB3 oncogenic unit and inhibits heregulin-induced activation of ErbB3," *Mol Cancer Ther*, 11:582-593, 2012.

Morrison, "Two heads are better than one," *Nat Biotechnol*, 25:1233-1234, 2007.

Orcutt et al., "A modular IgG-scFv bispecific antibody topology," *Protein Eng Des Sel*, 23:221-228, 2010.

Poovassery et al., Antibody targeting of HER2/HER3 signaling overcomes heregulin-induced resistance to PI3K inhibition in prostate cancer, *Int J Cancer*, 137:267-277, 2015.

Schoeberl et al., Therapeutically targeting ErbB3: A key node in ligand-induced activation of the ErbB receptor-PI3K axis, *Sci Signal*, 2:ra31, 2009.

Schoeberl et al., "An ErbB3 antibody, MM-121, is active in cancers with ligand-dependent activation," *Cancer Res*, 70:2485-2494, 2010.

Sergina et al., Escape from HER-family tyrosine kinase inhibitor therapy by the kinase-inactive HER3, *Nature*, 445:437-441, 2007.

Wilson et al., Widespread potential for growth-factor-driven resistance to anticancer kinase inhibitors, *Nature*, 487:505-509, 2012.

\* cited by examiner

TARGETING HER2 AND HER3 WITH BISPECIFIC ANTIBODIES IN CANCEROUS CELLS

CROSS REFERENCE TO RELATED APPLICATIONS

This application is a National Stage 371 Application of International Application No. PCT/US2014/063559, filed Oct. 31, 2014, which application claims priority to U.S. Provisional Patent Application 61/899,032, filed Nov. 1, 2013, all of which are herein incorporated by reference in their entirety.

INCORPORATION OF SEQUENCE LISTING

The sequence listing that is contained in the file named "UTSW007WO.txt," which is 25 kilobytes (as measured in Microsoft Windows®) and was created on Oct. 31, 2014, is filed herewith by electronic submission and is incorporated by reference herein.

FIELD OF THE INVENTION

The present invention relates to bispecific and monospecific tetravalent antibodies targeting HER2 and/or HER3, and methods for use thereof.

BACKGROUND OF THE INVENTION

Multiple cancers are driven by aberrant signaling through ErbB, or HER, family members. Recent studies have indicated that HER2-HER3 heterodimers can play a central role in tumorigenesis. HER3 is a preferred dimerization partner for HER2, which has no known ligand and is constitutively active. Although HER3 has very low intrinsic kinase activity, there are six phosphorylation dependent binding sites for PI3K on the cytosolic tail of this receptor. Consequently, HER2-HER3 heterodimers are the most effective activators identified to date of the PI3K/Akt pathway through both ligand-independent and ligand-dependent signaling. Ligand-dependent activation of HER3 involves the binding of heregulin or other ligands to induce a conformational switch in the dimerization arm, driving heterodimer formation with kinase competent partners such as HER2 or EGFR. Consistent with HER3 as a driver of tumorigenesis, loss of HER3 expression in breast cancer cells results in reductions in both PI3K/Akt signaling and proliferation (Lee-Hoeflich S T, Crocker L, Yao E, Pham T, Munroe X, Hoeflich K P, et al. A central role for HER3 in HER2-amplified breast cancer: implications for targeted therapy. *Cancer Res* 2008; 68:5878-87; and Holbro T, Beerli R R, Maurer F, Koziczak M, Barbas C F, 3rd, Hynes N E. The ErbB2/ErbB3 heterodimer functions as an oncogenic unit: ErbB2 requires ErbB3 to drive breast tumor cell proliferation. *Proc Natl Acad Sci USA* 2003; 100:8933-8). Further, modeling studies demonstrate that HER3 represents a central node in PI3K/Akt signaling. In conjunction with the limited efficacy of solely targeting HER2 with monotherapies such as trastuzumab these observations have motivated the development of therapeutics targeting HER3 and/or HER2-HER3 heterodimers. Recent data indicates that the targeting of this axis with antibodies is less effective in the presence of heregulin, which is expressed in either autocrine or paracrine fashion in many tumor types.

As an alternative to targeting HER family members with antibodies, the use of small molecule inhibitors of the tyrosine kinase activity of EGFR and/or HER2, or of the downstream kinase, PI3K, has attracted much interest. However, these inhibitors can lead to tumor escape due to upregulation of compensatory signaling pathways and complex cross-regulatory networks involving negative feedback loops. For example, the delivery of lapatinib, a tyrosine kinase inhibitor (TKI) that targets both EGFR and HER2, results in upregulation of HER2 and HER3 expression. Lapatinib resistance pathways can also include activating mutations of PI3K, and the inhibitory effects of lapatinib can be dampened by the presence of the HER3 ligand, heregulin. (Sergina N V, Rausch M, Wang D, Blair J, Hann B, Shokat K M, et al. Escape from HER-family tyrosine kinase inhibitor therapy by the kinase-inactive HER3. *Nature* 2007; 445:437-41; Wilson T R, Fridlyand J, Yan Y, Penuel E, Burton L, Chan E, et al. Widespread potential for growth-factor-driven resistance to anticancer kinase inhibitors. *Nature* 2012; 487:505-9 and Li Q, Ahmed S, Loeb J A. Development of an autocrine neuregulin signaling loop with malignant transformation of human breast epithelial cells. *Cancer Res* 2004; 64:7078-85). This suggests that lapatinib in combination with antibodies or bispecifics that bind to HER3 might provide an effective route for therapy, particularly for tumors involving autocrine or paracrine heregulin loops that can result in limited efficacy of monotherapies.

Related to the limited therapeutic efficacy of TKIs such as lapatinib that inhibit EGFR and HER2 activation, HER3 can associate with other activating receptors such as cMET and insulin-like growth factor type I receptor I/insulin receptor substrate-1. A possible strategy to extinguish HER3-PI3K signaling could therefore be to inhibit multiple potential HER3 partners.

Thus, there is a need for the generation of improved therapeutics directed towards ligand-dependent activation of HER3.

SUMMARY OF THE INVENTION

This invention pertains to bispecific antibody molecules (e.g. bs Ab) that can be used in the detection and/or treatment of various cancers that express HER3 (also known as ErbB3) and HER2. In particular, bispecific antibodies of the present invention and described compositions and methods may, in specific illustrative embodiments, reduce the proliferation of cancer mediated by one or more of HER3 ligands such as heregulin. In one embodiment, this invention provides a bispecific antibody that binds to HER3 and HER2 facilitating dimerization of HER2 and HER3, as well as inhibition of various HER3 and/or HER2 functions.

In some embodiments, bispecific antibody molecules of the present disclosure comprise an anti-HER2 antibody comprising two heavy chains and two light chains and an anti-HER3 single chain Fv connected (directly or through a linker) to the antibody at the CH3 domain. Any such fusion described herein may be made according to methods known in the art, which include genetic linkage of two proteins (fusion proteins) wherein one protein is connected via its N-terminus to the C-terminus of another protein. As is also known, an scFv or other protein, for example, can be fused to the N-terminus or the C-terminus of another protein. See Ahmad Z. A. et al., (Clinical and Developmental Immunology, Volume 2012 (2012), Article ID 980250). In certain embodiments, the anti-HER2 antibody is joined to the anti-HER3 single chain Fv, or the anti-HER3 antibody is joined to the anti-HER2 single chain Fv, by a linker, more preferably by a peptide linker, and most preferably by a peptide linker that lacks a proteolytic cleavage site. In various embodiments, the single chain Fv links to the CH3 domain of the anti-HER2 or HER3 antibody by a linker comprising a Gly-Ser-Ser sequence. In various embodiments, the single chain Fv comprises a (Gly$_4$Ser)$_n$ peptide linker, corresponding to SEQ ID NO: 11 and multiples thereof, between the light chain variable domain and the heavy chain variable domain of the anti-HER2 or HER3 single chain Fv. The antibody binds specifically to HER2 interfering with the function thereof and the single chain Fv binds specifically to HER3 and interfering with various functions thereof, or vice versa. In some embodiments, the bispecific antibody has a Morrison format. In some embodiments the HER2 antibody is trastuzumab.

In certain embodiments, the invention further provides bivalent single chain Fvs comprising two single chain Fvs, one specific for HER3 and the other specific for HER2. In certain aspects, the bivalent single chain Fv comprise two single chain Fvs connected to each other directly or through a linker. In further embodiments, the bivalent single chain Fvs are produced as a single peptide chain with two VH and two VL regions, yielding tandem single chain Fvs.

In further embodiments, the bispecific antibody molecules can be "diabodies," which are antibody fragments with two antigen-binding sites (one specific for HER3 and the other for HER2), comprising a VH domain connected to a VL domain in the same polypeptide chain. In certain aspects, a linker that is too short to allow pairing between the two domains on the same chain is used, and the domains are forced to pair with the complementary domains of another chain and create two antigen-binding sites (Holliger et al., (1993) *Proc. Natl. Acad. Sci.* 90: 6444-6448). In other embodiments, the bispecific antibody molecules of the present disclosure comprise bispecific triabodies or tetrabodies, which are multivalent but bispecific for HER2 and/or HER3. In certain embodiments, bispecific diabodies, triabodies, or tetrabodies comprise a non-covalent association of two or more single chain Fv molecules. In certain aspects, bispecific diabodies are heterodimers of different single chain Fvs, where each single chain Fv comprises the VH domain from the selected antibody connected by a short linker to the VL domain of the other antibody.

In further embodiments, the molecules of the present disclosure comprise monospecific tetravalent antibodies that comprise multiple binding sites, such as four, of monoclonal antibodies or single chain Fvs. In certain embodiments the antibodies or single chain Fvs are specific for HER3, and in particular embodiments, all monoclonal antibodies or single chain Fvs comprise the same HER3 epitope-binding site or are identical. In a particular embodiment, the present disclosure describes monospecific tetravalent antibodies, such as a tetravalent tetramer of single chain Fvs, resulting in four binding sites. In one embodiment, the monospecific tetravalent antibody is a monospecific tetravalent HER3 antigen binding antibody, comprising four single chain Fv monomers, wherein each VH of one of the single chain Fv monomers associates intermolecularly with each VL of the other single chain Fv monomer, thereby forming the monospecific tetravalent HER3 antigen binding antibody. Methods for producing triabodies and tetrabodies are described in, for example, Hudson et al., *Nat. Med.* 9:129-134 (2003). Multiple technologies exist for making a single antibody-like molecule that incorporates antigen specificity domains from two separate antibodies (bi-specific antibody). Suitable technologies have been described by Macrogenics (Rockville, Md.), Micromet (Bethesda, Md.) and Merrimack (Cambridge, Mass.). (See, e.g., Orcutt K D, Ackerman M E, Cieslewicz M, Quiroz E, Slusarczyk A L, Frangioni J V, Wittrup K D. A modular IgG-scFv bispecific antibody topology. Protein Eng Des Sel. (2010) 23:221-228; Fitzgerald J, Lugovskoy A. Rational engineering of antibody therapeutics targeting multiple oncogene pathways. MAbs. (2011) 1; 3(3); Baeuerle P A, Reinhardt C. Bispecific T-cell engaging antibodies for cancer therapy. Cancer Res. (2009) 69:4941-4944.) Production of a tetravalent bispecific antibody by fusion of, an IgG antibody format and single chain domains is described by Coloma, M. J., et. al., *Nature Biotech.* 15 (1997) 159-163; WO 2001/077342; and Morrison, S. L., *Nature Biotech.* 25 (2007) 1233-1234.

In certain embodiments, the bispecific antibody or polyspecific antibody is encoded by two vectors comprising nucleic acids that encode polypeptide sequences that are presented as SEQ ID NO: 1 and SEQ ID NO: 2, and in certain instances, the nucleic acids comprise a sequence that is presented by SEQ ID NO: 5 and SEQ ID NO: 6, respectively. In certain embodiments, the bispecific or polyspecific antibody is encoded by vectors comprising two nucleic acid sequences encoding polypeptides selected from the group consisting of SEQ ID NO: 1 and SEQ ID NO: 2. In certain instances, the two nucleic acid sequences are selected from the group consisting of SEQ ID NO: 5 and SEQ ID NO: 6. In certain instances the vectors further comprise nucleic acid sequences encoding polypeptides comprising the amino acid sequences of SEQ ID NO: 1 and SEQ ID NO: 2. Vectors and transformants comprising the nucleic acid sequences encoding the antibody, single chain Fv, and optionally the linker molecules are also provided. In certain embodiments, the antibody comprises the Fc portion and the single chain Fv comprising a heavy chain variable domain (VH) and a light chain variable domain (VL).

In certain embodiments, the antibody is tetravalent and is encoded by two vectors comprising nucleic acids that encode polypeptide sequences that are presented as SEQ ID NO: 3 and SEQ ID NO: 4, and certain instances, the nucleic acids comprise a sequence that is presented by SEQ ID NO: 7 and SEQ ID NO: 8, respectively. In other embodiments, the tetravalent or multivalent antibody is encoded by vectors comprising two nucleic acid sequences encoding polypeptides selected from the group consisting of SEQ ID NO: 3 and SEQ ID NO: 4. In certain instances, the two nucleic acid sequences are selected from the group consisting of SEQ ID NO: 7 and SEQ ID NO: 8. In certain instances the vectors further comprise nucleic acid sequences encoding polypeptides having the amino acid sequences of SEQ ID NO: 3 and SEQ ID NO: 4. In certain instances, the nucleic acid sequences are SEQ ID NO: 7 and SEQ ID NO: 8, respectively. Vectors and transformants comprising the nucleic acid sequences encoding the antibody, single chain Fv, and optionally the linker molecules are also provided. In certain embodiments, the antibody comprises the Fc portion and the single chain Fv comprising a heavy chain variable domain (VH) and a light chain variable domain (VL).

In certain embodiments, the bispecific antibody is of a Morrison-format comprising an anti-HER2 antibody comprising two heavy chains and two light chains and at least one anti-HER3 single chain Fv comprising a heavy chain variable domain and a light chain variable domain linked to any one of the two heavy chains or two light chains of the anti-HER2 antibody. In further embodiments, an anti-HER3 single chain Fv is linked to each heavy chain of the anti-HER2 antibody. The isolated monoclonal bispecific antibody facilitates formation of HER2-HER3 dimers during use. In various embodiments, the light chain variable domain of the anti-HER3 single chain Fv comprises 607-717 of SEQ ID NO: 1 or conservative amino acid substitutions thereof and the heavy chain variable domain of the anti-HER3 single chain Fv comprises 473-591 of SEQ ID NO: 1 or conservative amino acid substitutions thereof. In various embodiments, the light chain variable domain of the anti-HER2 antibody comprises an amino acid sequence 20-127 of SEQ ID NO: 2 or conservative amino acid substitutions thereof and the heavy chain variable domain of the anti-HER2 antibody comprises an amino acid sequence 20-139 of SEQ ID NO: 1 or conservative amino acid substitutions thereof.

In certain embodiments, the multivalent antibody is of a Morrison-format comprising an anti-HER3 antibody comprising two heavy chains and two light chains and at least one anti-HER3 single chain Fv comprising a heavy chain variable domain and a light chain variable domain linked to any one of the two heavy chains or two light chains of the anti-HER3 antibody. In further embodiments, an anti-HER3 single chain Fv is linked to each heavy chain of the anti-HER3 antibody. The isolated monoclonal tetravalent/multivalent internalizes HER3 more efficiently than the bivalent anti-HER3 antibody. In various embodiments, the light chain variable domain of the anti-HER3 single chain Fv comprises 606-716 of SEQ ID NO: 3 or conservative amino acid substitutions thereof and the heavy chain variable domain of the anti-HER3 single chain Fv comprises 472-590 of SEQ ID NO: 3 or conservative amino acid substitutions thereof. In various embodiments, the light chain variable domain of the anti-HER3 antibody comprises an amino acid sequence 20-131 of SEQ ID NO: 4 or conservative amino acid substitutions thereof and the heavy chain variable domain of the anti-HER3 antibody comprises an amino acid sequence 20-138 of SEQ ID NO: 3 or conservative amino acid substitutions thereof.

In various embodiments, when the described monoclonal antibodies are administered to cancer cells that are SK-BR-3 cells, BT-474 cells, or HCC1419 cells or other breast cancer cells, the proliferation is reduced by at least 25% relative to a control, at least 50% relative to a control or more.

In another embodiment, this invention includes a composition comprising a bispecific or polyspecific antibody as disclosed and/or claimed herein and a pharmaceutically acceptable carrier.

This invention also provides a method for treating cancer (e.g. mitigating one or more symptoms of cancer). The method typically involves administering to a patient (human or non-human animal) in need thereof a therapeutically effective amount of a bispecific or polyspecific antibody as disclosed and/or claimed herein and a pharmaceutically acceptable carrier. The cancer can include, but is not limited to a cancer selected from the group consisting of breast, colon, ovarian, endometrial, gastric, pancreatic, prostate and salivary gland cancer. The administration can be by any of a variety of convenient methods including systemic injectable administration, injection into a tumor or cancerous tissue, oral administration, and the like.

In still another embodiment, this invention provides a method for treating cancer (e.g. mitigating one or more symptoms of cancer). The method typically involves administering to a patient (human or non-human animal) in need thereof a therapeutically effective amount of a bispecific or polyspecific antibody as disclosed and/or claimed herein and a pharmaceutically acceptable carrier, in combination with another cytotoxic agent selected from the group consisting of a chemotherapeutic agent, external beam radiation, a targeted radioisotope, signal transduction inhibitor and a tyrosine kinase inhibitor, such as lapatinib or erlotinib. The cancer can include, but is not limited to a cancer selected from the group consisting of breast, colon, ovarian, endometrial, gastric, pancreatic, prostate and salivary gland cancer. The administration can be by any of a variety of convenient methods including systemic injectable administration, injection into a tumor or cancerous tissue, oral administration, and the like.

In yet another embodiment, this invention provides a chimeric moiety comprising of a bispecific or polyspecific antibody as disclosed and/or claimed herein coupled to an effector. Preferred effectors include, but are not limited to a cytotoxin, a label, a radionuclide, a drug, a liposome, a ligand, and an antibody. In certain instances, where the effector is a polypeptide, the chimeric moiety is a fusion protein, preferably a recombinantly expressed fusion protein. This invention also provides a method of specifically delivering or targeting an effector molecule to a cell bearing a HER3 or HER2 receptor. The method involves providing a chimeric moiety as described and/or claimed herein, and contacting the cell with the chimeric moiety, whereby the chimeric moiety specifically binds to the cell. In certain embodiments, the chimeric moiety is a fusion protein. In certain embodiments, the cell is a cancer cell, preferably a cancer cell that expresses HER3. Particularly preferred cancer cells include, but are not limited to breast, colon, ovarian, endometrial, gastric, pancreatic, prostate and salivary gland cancer cells.

Also provided is a method of specifically killing and/or inhibiting the growth or proliferation of a cell bearing a HER3 receptor. The method typically involves providing a chimeric moiety as described and/or claimed herein attached to a cytotoxic or cytostatic effector (e.g. a cytotoxin, a radioactive moiety, and a liposome comprising a cytotoxic or cytostatic agent, and the like); and contacting said cell with the chimeric moiety, whereby the chimeric moiety specifically binds to the cell resulting in the death and/or inhibition of growth and/or proliferation of the cell. In certain embodiments, the chimeric moiety is a fusion protein. In certain embodiments, the cell is a cancer cell, preferably a cancer cell that expresses HER3. Particularly preferred cancer cells include, but are not limited to breast, colon, ovarian, endometrial, gastric, pancreatic, prostate and salivary gland cancer cells.

This invention also provides methods of detecting and/or visualizing and/or diagnosing the presence of a cancer cell or tissue. The method typically involves contacting a cell or tissue with a bispecific or polyspecific antibody as described herein attached to a detectable label; and detecting the label where detection of the label in association with the cell or tissue indicates the presence of a cell or tissue expressing (including overexpressing) HER3 and/or HER2. Preferred detectable labels include, but are not limited to a gamma emitter, a positron emitter, an MRI label, and a fluorescent or colorimetric label. In certain instances, the detectable label is a gamma emitter and the detection comprises imaging with a gamma camera. In certain instances, the detectable label is a positron emitter and the detection comprises imaging with positron emission tomography (PET). In certain instances, the detectable label is an MRI label and the detection comprises detecting with magnetic resonance imaging. The cell or tissue can be a cancer cell or tissue (e.g., breast, colon, ovarian, endometrial, gastric, pancreatic, prostate, or salivary gland cancer). It is noted that the diagnostic assay can be a component of a differential diagnosis of a cancer and/or can be used to type a cancer as one that expresses HER3 and/or HER2 and/or the assay can be used to visualize a known cancer. In these (and other) instances, the assay need not be dispositive of the presence of a cancer cell, but simply indicative of the likely presence of such a cell or tissue. In certain embodiments, the detection comprises a non-invasive imaging technique. In certain embodiments, the detection comprises immunohistochemistry. In certain embodiments, the detection comprises detecting in a tissue sample or biopsy. In certain embodiments, the detection comprises detecting in a tissue section. In certain embodiments, the detection is in vivo detection.

The terms "a" and "an" are defined as one or more unless this disclosure explicitly requires otherwise.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, the methods and systems of the present invention that "comprises," "has," "includes" or "contains" one or more elements possesses those one or more elements, but is not limited to possessing only those one or more elements. Likewise, an element of a method or system of the present invention that "comprises," "has," "includes" or "contains" one or more features possesses those one or more features, but is not limited to possessing only those one or more features.

Furthermore, a structure that is capable of performing a function or that is configured in a certain way is capable or configured in at least that way, but may also be capable or configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any composition, method, or system of the present invention can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

FIG. 4A, cells were incubated with 50 nM anti-HER3 (Ab6), tetrameric anti-HER3 (Ab6tet), trastuzumab (T), pertuzumab (P), trastuzumab or pertuzumab and Ab6 (T+Ab6 or P+Ab6), bispecific trastuzumab with anti-HER3 Ab6 scFv (TAb6), or bispecific pertuzumab with anti-HER3 Ab6 scFv (PAb6) for 5 days. Proliferative responses were assessed using the MTS reagent and were normalized against the proliferation of cells incubated in medium (Med) only. Data shown are means of triplicates±standard deviation. * and ** indicate significantly lower or higher proliferative responses, respectively, between cells treated with antibody and PBS vehicle (Student's t test; p<0.05). FIG. 4B, SK-BR-3 or BT-474 cells were treated with anti-HER2/HER3 antibodies (50 nM) for 1 or 24 hours, and cell lysates analyzed by immunoblotting. Data shown are representative of at least two independent experiments.

Akt signaling in the presence of heregulin. FIG. 8A, Cells were incubated with heregulin (HRG, 6.25 nM) and 50 nM anti-HER3 (Ab6), tetrameric anti-HER3 (Ab6tet), trastuzumab (T), trastuzumab and Ab6 (T+Ab6) or bispecific trastuzumab with anti-HER3 Ab6 scFv (TAb6) for 5 days. Proliferative responses were assessed using the MTS reagent and were normalized against the proliferation of cells incubated in medium (Med) only. Data shown are means of triplicates±standard deviation. * indicates statistically significant differences between proliferative responses for cells treated with antibody in the presence of heregulin and cells treated with heregulin only (Student's t test; p<0.05). FIG. 8B, SK-BR-3 or BT-474 cells were treated with anti-HER2/HER3 antibodies (50 nM) in the presence of 6.25 nM heregulin for 1 or 24 hours, and cell lysates analyzed by immunoblotting. Data shown are representative of at least two independent experiments.

FIG. 9A, cells were incubated with different concentrations of lapatinib (L) in the presence and absence of heregulin (HRG; 6.25 nM) for 5 days. Proliferative responses were assessed using the MTS reagent and were normalized against the proliferation of cells incubated in medium (Med) only. Data shown are means of triplicates±standard deviation. * indicates statistically significant differences between proliferative responses for cells treated with lapatinib and DMSO vehicle (Student's t test; p<0.001). FIG. 9B, SK-BR-3 or BT-474 cells were treated with 1 μM lapatinib (Lap) in the presence and absence of heregulin (6.25 nM) for 1 or 24 hours, and cell lysates analyzed by immunoblotting. Data shown are representative of at least two independent experiments.

FIG. 11A, cells were incubated with 1 μM lapatinib (L) in the presence of heregulin (HRG; 6.25 nM) and treated with 50 nM anti-HER3 (Ab6), tetrameric anti-HER3 (Ab6tet), trastuzumab (T), trastuzumab and Ab6 (T+Ab6) or bispecific trastuzumab with anti-HER3 Ab6 scFv (TAb6) for 5 days. Proliferative responses were assessed using the MTS reagent and were normalized against the proliferation of cells incubated in medium (Med) only. Data shown are means of triplicates±standard deviation. * indicates statistically significant differences between proliferative responses for cells treated with antibodies vs. vehicle in the presence of lapatinib and heregulin (Student's t test; p<0.05). ** indicates statistically significant differences between the proliferative responses for the pairwise comparison of the two indicated treatments (horizontal bars). FIG. 11B, SK-BR-3 or BT-474 cells were treated with lapatinib (Lap), heregulin (6.25 nM) and anti-HER2/HER3 antibodies (50 nM) as indicated for 1 or 24 hours, and cell lysates analyzed by immunoblotting. Data shown are representative of at least two independent experiments.

DETAILED DESCRIPTION OF THE INVENTION

Figure 1:
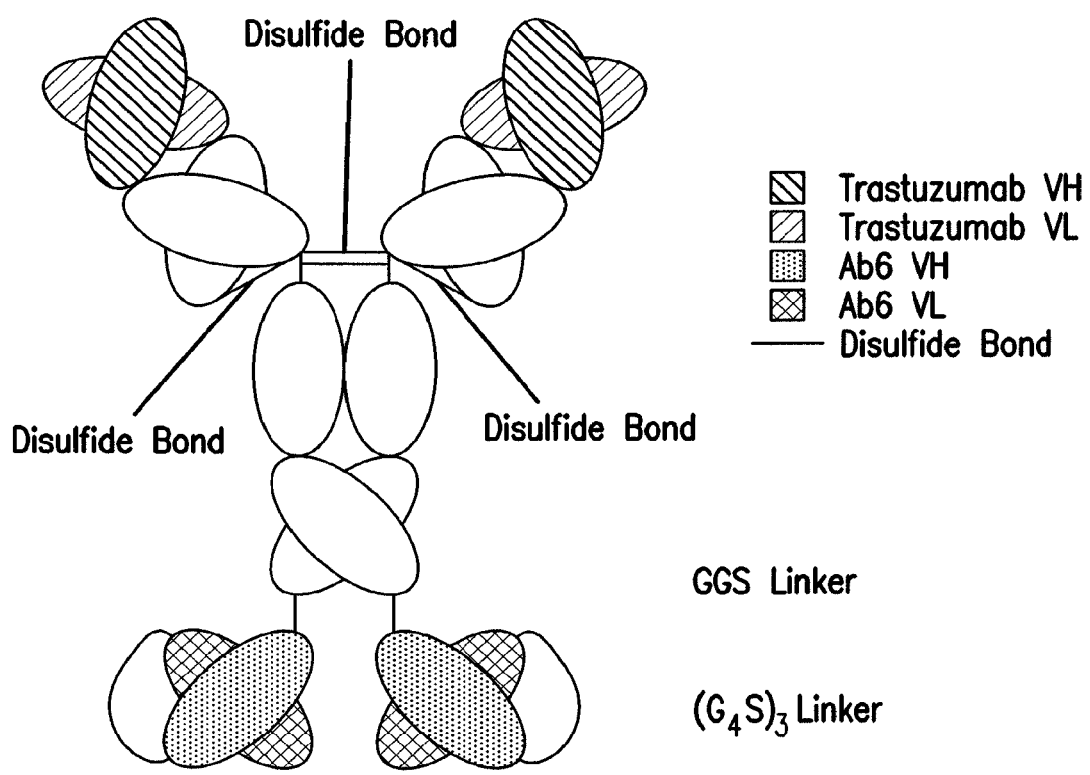
FIG. 1: Schematic representation of the bispecific antibody (TAb6) comprising trastuzumab and a single chain Fv derived from the anti-HERS antibody, Ab6, used in the current study.

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

The anti-HER2/HER3 bispecific antibody molecules of the present disclosure avoids the complexity of identifying and globally inhibiting all HER3 partners. Here the inventors have discovered the ability of a bispecific anti-HER2/HER3 antibody to drive HER3 into HER2-HER3 heterodimers that, through combination treatment with lapatinib, are 'kinase-dead'. Locking HER3 into such inactive complexes is expected to sequester this receptor from interactions with other signaling competent partners and, as such, have anti-tumor effects.

Other aspects of the disclosure comprise extinguishing HER3 signaling by inducing the efficient internalization and degradation of this receptor. For example, a multivalent (tetrameric) anti-HER3 antibody would induce more efficient HER3 internalization and/or degradation relative to its bivalent counterpart, thereby enhancing clearance from the cell surface. The efficacy of this approach has been compared with that of recruiting HER3 into kinase inactivated HER2-HER3 heterodimers. These comparative studies have also been extended to microscopy analyses of the trafficking behavior of the different antibodies within cells, which relates to both drug delivery for antibody-drug conjugates and Fc-mediated cytotoxicity.

Preparation of Bispecific Antibody Molecules:

The described antibodies can be prepared using a variety of methods. For example, the antibodies can be prepared separately (e.g. using chemical protein synthesis, recombinant expression methods, hybridoma technology, etc.) and then chemically attached to each other, either directly or through a linker. Means of chemically conjugating molecules are well known to those of skill in the art. The procedures for chemically coupling two antibodies are straightforward. Polypeptides typically contain a variety of functional groups; e.g., carboxylic acid (COOH) or free amine (—NH2) groups, that are available for reaction with suitable functional groups on the corresponding antibody or on a linker.

Alternatively, the antibodies can be derivatized to expose or attach additional reactive functional groups. The derivatization can involve attachment of any of a number of linker molecules such as those available from Pierce Chemical Company, Rockford Ill. A variety of suitable linkers are known to those of skill in the art (see, e.g., European Patent Application No. 188,256; U.S. Pat. Nos. 4,671,958, 4,659, 839, 4,414,148, 4,699,784; 4,680,338; 4,569,789; and 4,589, 071; and Borlinghaus et al. (1987) Cancer Res. 47: 4071-4075) and suitable linkers are also described below with respect to the coupling of effectors to bispecific antibodies.

In certain preferred embodiments of the invention, the bispecific or tetravalent antibody molecules are produced by expression of recombinant antibody fragments in host cells. The scFv can be connected (directly or through a linker) to the full length antibody at the CH3 domain via either the N' or C' terminus of the scFv. The resulting nucleic acid molecules encoding the bispecific-antibody are inserted into expression vectors and introduced into host cells. The resulting bispecific antibody molecules are then isolated and purified from the expression system.

In certain embodiments of the invention, the scFv antibody molecules can be paired together with a novel linker molecule designed to protect against proteolytic degradation of the bispecific or tetravalent scFv antibody molecules. Such a linker typically lacks a proteolytic cleavage site.

The purity of the bispecific or tetravalent antibody molecules of the invention may be assessed using standard methods known to those of skill in the art, including, but not limited to, ELISA, immunohistochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

Using the antibodies, nucleic acid sequences, and other teaching provided herein, bispecific or tetravalent antibodies of this invention can be recombinantly expressed using routine methods such as those set forth in Sambrook et al. (1989) Molecular Cloning, Cold Spring Harbor Laboratory, or Ausubel et al. (eds) (1997) Current Protocols in Molecular Biology, John Wiley & Sons N.Y. In addition illustrative methods of producing recombinant bispecific or tetravalent scFvs of this invention are set forth in the Examples. To the extent that specific materials are mentioned, it is merely for purposes of illustration and is not intended to limit the invention.

Administration of Bs-scFv Antibody Molecules:

A) Pharmaceutical Formulations.

Bispecific or tetravalent antibodies, as described herein, include bulk drug compositions useful in the manufacture of non-pharmaceutical compositions (e.g., impure or non-sterile compositions), and pharmaceutical compositions (i.e., compositions that are suitable for administration to a subject or patient i.e., human or non-human subject) that can be used directly and/or in the preparation of unit dosage forms. In certain embodiments, such compositions comprise a therapeutically effective amount of one or more therapeutic agents (e.g. bispecific and/or tetravalent antibodies, and/or chimeric moieties comprising such antibodies) and a pharmaceutically acceptable carrier.

As indicated above, the agents of this invention can be used in a wide variety of contexts including, but not limited to the detection and/or imaging of tumors or cancer cells, inhibition of tumor growth and/or cancer cell growth and/or proliferation, and the like. One or more bispecific or tetravalent antibodies, and/or functionalized bispecific or tetravalent antibodies, and/or chimeric moieties of this invention can be administered by injection, that is, intravenously, intramuscularly, intracutaneously, subcutaneously, intraduodenally, or intraperitoneally. Also, in certain embodiments, the compounds can be administered by inhalation, for example, intranasally. Additionally, certain compounds can be administered orally.

In a specific embodiment, the term "pharmaceutically acceptable" means formulated for use in animals, and more particularly in humans, or suitable for administration to an animal or human and in one embodiment refers to compositions approved or approvable by a regulatory agency of the Federal or a state government or listed in the U.S. Pharmacopeia or other generally recognized pharmacopeia for use in animals, including humans. The term "carrier" refers to a pharmaceutically acceptable carrier that can be administered to a subject, together with the antibody molecules of the present disclosure, and which does not destroy the pharmacological activity thereof and is nontoxic when administered in doses sufficient to deliver a therapeutic amount. In certain aspects, a pharmaceutically acceptable carrier may comprise any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In certain aspects, it is preferable to include isotonic agents, for example, sugars, polyalcohols such as mannitol, sorbitol, or sodium chloride in the composition. Additional examples of pharmaceutically acceptable carriers are wetting agents or minor amounts of auxiliary substances such as wetting or emulsifying agents, preservatives or buffers, which enhance the shelf life or effectiveness of the antibody molecule of the present disclosure. In certain aspects, a pharmaceutically acceptable carrier may comprise any pharmaceutical agent that does not itself induce the production of an immune response harmful to a subject receiving the composition, and which may be administered without undue toxicity. In certain aspects, pharmaceutically acceptable carriers include saline and aqueous buffer solutions.

In certain embodiments, a "pharmaceutical composition" comprises a pharmaceutically acceptable carrier and an antibody molecule according to the invention. The pharmaceutical compositions may comprise one or more pharmaceutically acceptable sterile isotonic aqueous or nonaqueous solutions, dispersions, suspensions or emulsions, or sterile powders, which can be reconstituted into sterile injectable solutions or dispersions just prior to use. Such pharmaceutical compositions can contain antioxidants; buffers; bacteriostats; solutes, which render the formulation isotonic with the blood of the intended recipient; suspending agents; thickening agents; preservatives; and the like.

The compositions of the invention can be provided as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Pharmaceutical compositions comprising the bispecific or tetravalent antibodies, and/or functionalized bispecific or tetravalent antibodies, and/or chimeric moieties of this invention can be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries that facilitate processing of the molecules into preparations that can be used pharmaceutically. Proper formulation is dependent upon the route of administration chosen.

For injection, the bispecific or tetravalent antibodies, and/or functionalized bispecific or tetravalent antibodies, and/or chimeric moieties of this invention can be formulated in aqueous solutions, preferably in physiologically compatible buffers such as Hanks's solution, Ringer's solution, or physiological saline buffer. The solution can contain formulatory agents such as suspending, stabilizing and/or dispersing agents. Alternatively, compositions comprising the iron chelating agent(s) can be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the bispecific or tetravalent antibodies, and/or functionalized bispecific or tetravalent antibodies, and/or chimeric moieties of this invention can be readily formulated by combining the agent(s) with pharmaceutically acceptable carriers well known in the art. Such carriers enable the agent(s) to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added.

For buccal administration, the iron chelating agent(s) can take the form of tablets, lozenges, etc. formulated in conventional manner.

For administration by inhalation, bispecific or tetravalent antibodies, and/or functionalized bispecific or tetravalent antibodies, and/or chimeric moieties of this invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator may be formulated containing a powder mix of the iron chelating agent(s) and a suitable powder base such as lactose or starch.

In addition to the formulations described previously, the bispecific or tetravalent antibodies, and/or functionalized bispecific or tetravalent antibodies, and/or chimeric moieties of this invention can also be formulated as a depot preparation. Such long acting formulations may be administered by implantation (for example subcutaneously or intramuscularly) or by intramuscular injection. Thus, for example, the agent(s) of this invention can be formulated with suitable polymeric or hydrophobic materials (for example as an emulsion in an acceptable oil) or ion exchange resins, or as sparingly soluble derivatives, for example, as a sparingly soluble salt.

Other pharmaceutical delivery systems can also be employed. Liposomes and emulsions are well known examples of delivery vehicles that may be used to deliver the bispecific or tetravalent antibodies, and/or functionalized bispecific or tetravalent antibodies, and/or chimeric moieties of this invention. Certain organic solvents such as dimethylsulfoxide also may be employed, although usually at the cost of greater toxicity. Additionally, the bispecific or tetravalent antibodies, and/or functionalized bispecific or tetravalent antibodies, and/or chimeric moieties of this invention can be delivered using a sustained-release system, such as semipermeable matrices of solid polymers containing the therapeutic agent. Various sustained-release materials have been established and are well known by those skilled in the art. Sustained-release capsules may, depending on their chemical nature, can release the active agent(s) for a few days, a few weeks, or up to over 100 days. Depending on the chemical nature and the biological stability of the agent(s) additional strategies for stabilization can be employed.

As the bispecific or tetravalent antibodies, and/or functionalized bispecific or tetravalent antibodies, and/or chimeric moieties of this invention may contain charged side chains or termini, they can be included in any of the above-described formulations as the free acids or bases or as pharmaceutically acceptable salts. Pharmaceutically acceptable salts are those salts which substantially retain the biological activity of the free bases and which are prepared by reaction with inorganic acids. Pharmaceutical salts tend to be more soluble in aqueous and other protic solvents than are the corresponding free base forms.

B) Effective Dosages.

The bispecific or tetravalent antibodies, and/or functionalized bispecific or tetravalent antibodies, and/or chimeric moieties of this invention will generally be used in an amount effective to achieve the intended purpose (e.g. to image a tumor or cancer cell, to inhibit growth and/or proliferation of cancer cells, etc.). In certain preferred embodiments, the bispecific or tetravalent antibodies, and/or functionalized bispecific or tetravalent antibodies, and/or chimeric moieties utilized in the methods of this invention are administered at a dose that is effective to partially or fully inhibit cancer cell proliferation and/or growth, or to enable visualization of a cancer cell or tumor characterized by expression of HER2 and HER3. In certain embodiments, dosages are selected that inhibit cancer cell growth and/or proliferation at the 90%, more preferably at the 95%, and most preferably at the 98% or 99% confidence level. Preferred effective amounts are those that reduce or prevent tumor growth or that facilitate cancer cell detection and/or visualization. With respect to inhibitors of cell growth and proliferation, the compounds can also be used prophylactically at the same dose levels.

Typically, bispecific or tetravalent antibodies, and/or functionalized bispecific or tetravalent antibodies, and/or chimeric moieties of this invention, or pharmaceutical compositions thereof, are administered or applied in a therapeutically effective amount. A therapeutically effective amount is an amount effective to reduce or prevent the onset or progression (e.g, growth and/or proliferation) of a cancer cell and/or a tumor. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the IC50 as determined in cell culture. Such information can be used to determine useful doses in humans.

Initial dosages can also be estimated from in vivo data, e.g., animal models, using techniques that are well known in the art. One skilled in the art could readily optimize administration to humans based on animal data.

Dosage amount and interval can be adjusted individually to provide plasma levels of the inhibitors which are sufficient to maintain therapeutic effect.

Dosages for typical therapeutics are known to those of skill in the art. Moreover, such dosages are typically advisorial in nature and may be adjusted depending on the particular therapeutic context, patient tolerance, etc. Single or multiple administrations of the compositions may be administered depending on the dosage and frequency as required and tolerated by the patient.

In certain embodiments, an initial dosage of about 1 μg, preferably from about 1 mg to about 100 mg per kilogram daily will be effective. A daily dose range of about 5 to about 75 mg per kilogram is preferred. The dosages, however, can be varied depending upon the requirements of the patient, the severity of the condition being treated, and the compound being employed. Determination of the proper dosage for a particular situation is within the skill of the art. Generally, treatment is initiated with smaller dosages that are less than the optimum dose of the compound. Thereafter, the dosage is increased by small increments until the optimum effect under the circumstance is reached. For convenience, the total daily dosage can be divided and administered in portions during the day if desired. Any effective dosage may be used. Dosages may be routinely optimized according to well known methods in the art in view of the present disclosure and may be, for example, from about 0.1 to about 500 mg/kg and more typically, from about 0.1 to about 100 mg/kg, and ideally about 25 to about 50 mg/kg.

In cases of local administration or selective uptake, the effective local concentration of the bispecific antibodies and/or chimeric molecules may not be related to plasma concentration. One skilled in the art will be able to optimize therapeutically effective local dosages without undue experimentation. The amount of antibody and/or chimeric moiety will, of course, be dependent on the subject being treated, on the subject's weight, the severity of the affliction, the manner of administration and the judgment of the prescribing physician.

The therapy can be repeated intermittently. In certain embodiments, the pharmaceutical preparation comprising the bispecific antibody molecules can be administered at appropriate intervals, for example, once every week, once every two weeks, once every three weeks, or once every four weeks, until the pathological symptoms are reduced or alleviated, after which the dosage may be reduced to a maintenance level as desired. The appropriate interval in a particular case would normally depend on the condition of the patient. The therapy can be provided alone or in combination with other drugs, and/or radiotherapy, and/or surgical procedures.

C) Toxicity.

Preferably, a therapeutically effective dose of bispecific antibodies, and/or functionalized bispecific antibodies, and/or chimeric moieties of this invention described herein will provide therapeutic benefit without causing substantial toxicity.

Toxicity of the agents described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. Agents that exhibit high therapeutic indices are preferred. Data obtained from cell culture assays and animal studies can be used in formulating a dosage range that is not toxic for use in human. The dosage of the bispecific or tetravalent antibodies, and/or functionalized bispecific or tetravalent antibodies, and/or chimeric moieties of this invention preferably lie within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition (see, e.g., Fingl et al. (1975) In: The Pharmacological Basis of Therapeutics, Ch. 1, p. 1).

D) Kits.

The present invention further encompasses kits for use in detecting cells expressing or overexpressing HER2/HER3 in vivo, and/or in biological samples. Kits are also provided for inhibiting the growth and/or proliferation of cells expressing or overexpressing HER3 (e.g. cancer cells).

In certain embodiments, the kits comprise one or more bispecific or tetravalent antibodies. Depending on the use, the antibodies can be functionalized with linkers and/or chelators for coupling to an effector (e.g. a radioactive moiety, a liposome, a cytoxin, another antibody, etc.) as described herein.

In certain embodiments, the kits can comprise described bispecific or tetravalent antibodies as well as buffers and other compositions to be delivered to cells.

The kits can also include instructional materials teaching the use of the antibodies for detecting, e.g. cancer cells, and/or teaching the combination of the antibodies with functionalizing reagents or teaching the use of functionalized antibodies for imaging and/or therapeutic applications. In certain embodiments, the antibody is provided functionalized with a linker and/or a chelator (in one container) along with one or more effectors, e.g. cytotoxins, radioactive labels (in a second container) such that the two components can be separately administered (e.g. in pre-targeting approaches) or such that the two components can be administered shortly before use.

Certain instructional materials will provide recommended dosage regimen, counter indications, and the like. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Cell Lines, Reagents, and Antibodies

The human breast cancer cell lines BT-474 and SK-BR-3 were obtained from the American Type Culture Collection (ATCC, catalog nos. HTB-20 and HTB-30, respectively) and cultured in Hybricare Medium (ATCC, catalog no. 46-X) and McCoy's 5a (Gibco, catalog no. 12330-031/ Hyclone, catalog no. SF30200.01), with 1% penicillin/streptomycin and 10% FCS), respectively. The human breast cancer cell line HCC1419 (a generous gift of Drs. Adi Gazdar, John Minna and Kenneth Huffman, Hamon Center for Therapeutic Oncology Research, University of Texas Southwestern Medical Center at Dallas, Dallas, Tex.) was cultured in RPMI 1640 with 1% penicillin/streptomycin and 5% FCS.

For imaging experiments, cells were cultured in phenol-red free DMEM (Gibco, catalog no. 31053-028) supplemented with 1% penicillin/streptomycin, 1% L-Glutamine, 10 mM HEPES buffer, 1 mM sodium pyruvate, 100 nM MEM non-essential amino acids, 55 nM 2-mercaptoethanol and 10% FCS.

Polyclonal antibodies specific for phospho-Akt-T308 (catalog no. 9275S), Akt, phospho-Erk1,2 (catalog no. 9101S), Erk1,2 (catalog no. 9102S), phospho-HER2 Y1221/ 1222 (catalog no. 2249S), and monoclonal antibodies against phospho-Akt-5473 (D9E) (catalog no. 4060L), and phospho-HER3 Y1289 (D1B5) (catalog no. 2842) were obtained from Cell Signaling Technologies. Polyclonal anti-HER3 antibody (C-17) (catalog no. SC-285) was from Santa Cruz Biotechnology and monoclonal anti-c-erbB2 antibody (Ab-3 3B5) (catalog no. OP15L) was from Millipore. The monoclonal anti-actin antibody (Ab-5) (catalog no. 612656) was from BD Bioscience. Horseradish peroxidase-labeled goat anti-rabbit and anti-mouse IgG (H+L) (catalog nos. 111-035-003 and 115-035-003, respectively) were purchased from Jackson Immunoresearch Laboratories. Lapatinib (catalog no. L-4804) was obtained from LC Laboratories and recombinant human heregulin-β1 (HRG-β1; EGF-like domain, catalog no. 100-03) was obtained from Peprotech.

The methodology used to determine HER2 and HER3 levels by flowcytometry is as follows, unless otherwise indicated. Antibodies were labeled with either Alexa Fluor® 647 carboxylic acid, succinimidyl ester (Life Technologies, Catalog # A-20173) or Alexa Fluor® 488 carboxylic acid, succinimidyl ester (Life Technologies, Catalog # A-10235) using methods recommended by the manufacturer. Following the labeling reaction, antibodies were extensively dialyzed against PBS to remove unincorporated Alexa dye. Cells were seeded at a density of 100,000 cells per well in 24 well plates, incubated overnight, and subsequently treated with either 1 µM lapatinib or vehicle control (DMSO) for 24 hours at 37° C. in a $CO_2$ incubator. Treated cells were incubated with Alexa 647-labeled Ab6 and Alexa 488-labeled trastuzumab (50 nM each) for 15 minutes at 37° C. in a $CO_2$ incubator. Following incubation, cells were trypsinized, washed, and suspended in PBS. Stained cells were analyzed using a BD FACScalibur and data processed using FlowJo (Tree Star).

Example 2

Recombinant Antibodies

Clinical grade trastuzumab and pertuzumab were obtained from the UT Southwestern Pharmacy. For comparative purposes, trastuzumab and pertuzumab were also expressed in recombinant form using the same expression host as the other antibodies used in this study. Expression plasmids for the production of antibodies in stably transfected CHO cells were generated as follows: the genes encoding the heavy and light chain variable domains (VH and VL, respectively) of trastuzumab, pertuzumab and Ab6 (US patent 20100266584A1; MM-121) were synthesized commercially (Integrated DNA Technology, Genscript, or Thermo Fisher) and used to generate full length human IgG1 and human kappa genes with the leader peptide (MGWSCI-ILFLVATATGVHS) (SEQ ID NO: 9) from the anti-lysozyme antibody, Hulys10, using standard methods of molecular biology. The vectors pcDNA 3.3 TOPO and pOptiVEC-TOPO (OptiCHO Ab Express Kit, Life Technologies, catalog nos. K8300-01 and 12744017, respectively) were used for the expression of the light and heavy chain genes, respectively.

Figure 15:
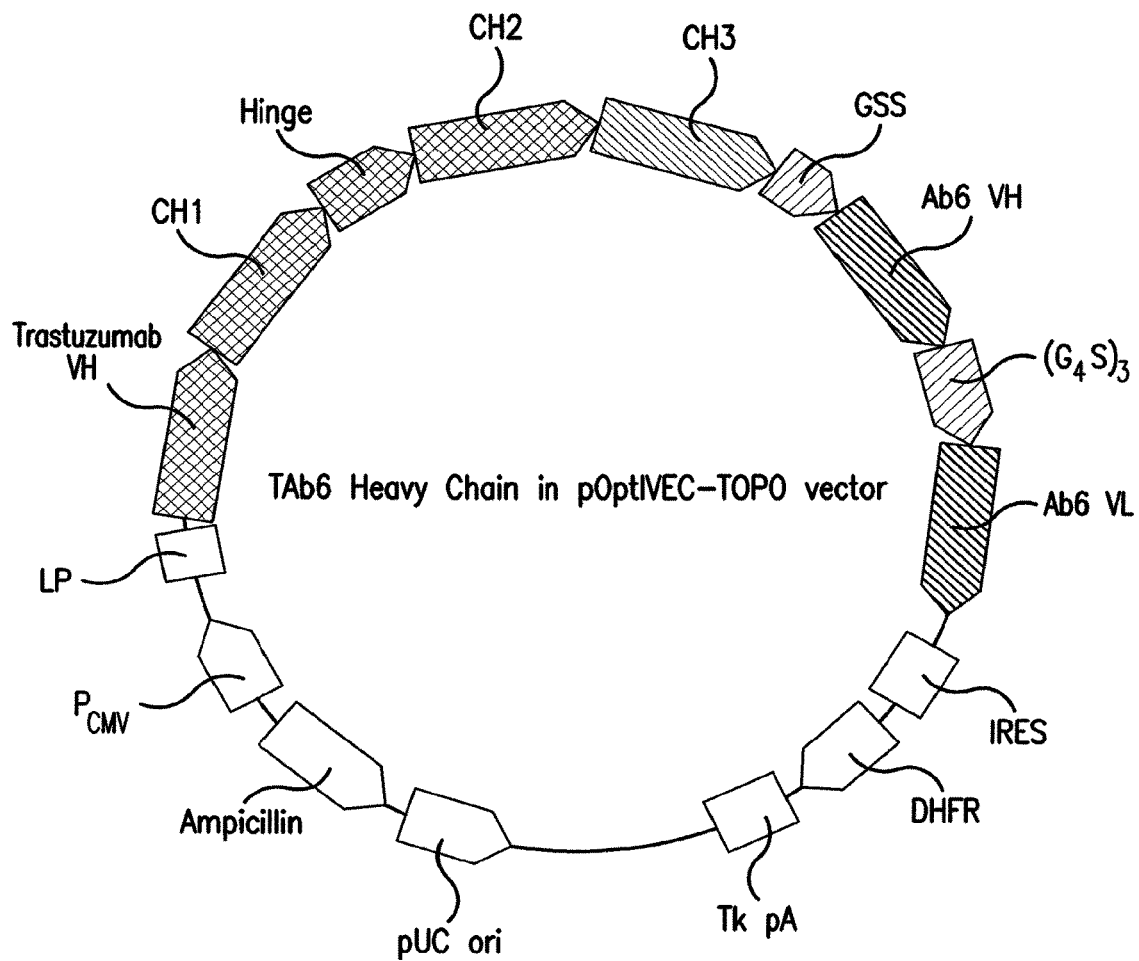
FIG. 15: A plasmid vector map for the TAb6 Heavy Chain gene.
Figure 16:
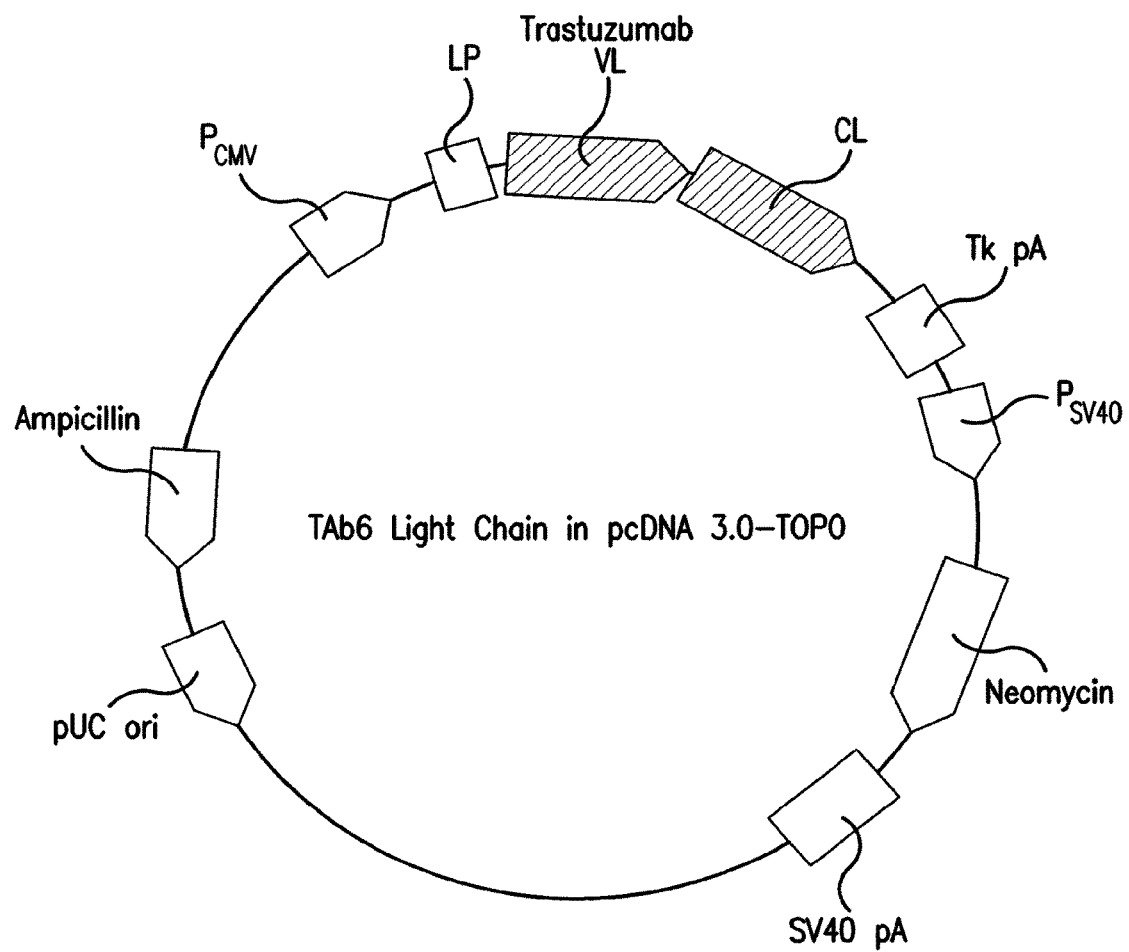
FIG. 16: Vector map of the TAb6 Light Chain gene.

To generate expression constructs for bispecific antibodies, a linker sequence containing a unique XhoI site was inserted at the 3' end of the heavy chain genes (trastuzumab and pertuzumab) using a designed oligonucleotide and the PCR. A scFv gene encoding the Ab6 scFv with codons encoding a $(Gly_4Ser)_3$ (SEQ ID NO: 10) linker peptide between the VH (JH) and VL gene was generated using standard methods of molecular biology. XhoI sites and Gly-Ser-Ser codons to connect the CH3 domain to the VH gene, were appended to the 5' and 3' ends of the scFv gene using the PCR. This scFv gene was cloned into the XhoI sites at the 3' ends of the trastuzumab and pertuzumab heavy chain genes to generate full length heavy chains linked to the Ab6 scFv. SEQ ID NO: 1 represents the heavy chain nucleotide and corresponding amino acid sequences for TAb6 and SEQ ID NO: 2 represents the light chain nucleotide and corresponding amino acid sequences for TAb6. A map of the TAb6 heavy chain plasmid vector and a map of the TAb6 light chain plasmid vector gene are illustrated in FIG. 15 and FIG. 16, respectively.

Example 3

Transfections and Expression of Recombinant Antibodies

Light chain expression constructs were transfected into CD/DG44 CHO cells (Life Technologies, catalog no. A11000-01) using electroporation. Desired clones were selected in CD/DG44 CHO medium (Life Technologies, catalog no. 12610010) containing 500 µg/ml geneticin without the HT supplement. The clone expressing the highest levels of light chain was identified by screening culture supernatants with ELISAs using goat anti-human kappa light chain antibody for detection (Sigma-Aldrich, catalog no. A7164). Heavy chain expression constructs were then transfected into their respective stably transfected light chain expressing CD/DG44 CHO clones via electroporation and selected with Opti-CHO Medium (Life Technologies, catalog no. 12681-011) containing 500 µg/ml geneticin. Supernatants of clones were screened by sandwich ELISA using goat anti-human IgG (Fab specific, Sigma-Aldrich, catalog no. 15260) as capture antibody and goat anti-human IgG (Fc-specific) conjugated to horseradish peroxidase (Sigma-Aldrich, catalog no. A0170) as detection antibody. The clones expressing the highest levels of antibody were expanded and cultured in increasing concentrations of methotrexate (MTX, 50 nM-4 µM) to induce gene amplification. Clones were further expanded in shake flasks (130 rpm) in 8% $CO_2$ and antibody purified from culture supernatants using protein G-Sepharose (GE Healthcare, catalog no. 17-0618-05). Several antibodies were also scaled up and purified by BioXCell.

Example 4

Proliferation Assays

Cells were plated in 96 well plates at a density of 2,500 cells per well and incubated overnight. Cells were treated with lapatinib (1 µM), HRG-β1 (6.25 nM), anti-HER3 antibody Ab6 or the tetrameric form, Ab6tet, trastuzumab (anti-HER2), pertuzumab (anti-HER2), or the bispecific anti-HER2/HER3 antibodies TAb6 and PAb6 as indicated in the figure legends. Antibodies were used at a concentration of 50 nM unless otherwise indicated. Dimethyl sulfoxide or phosphate buffered saline (PBS) were used as vehicle controls for lapatinib or HRG-β1/antibodies, respectively. After 5 days of incubation in a 37° C. 5% $CO_2$ incubator, cell proliferation was quantitated using CellTiter 96 AQeous One Solution Proliferation Assay kit (Promega, catalog no. G3580) according to the manufacturer's instructions.

Example 5

Immunoblotting

Cells cultured to near confluence in 6 well plates were treated with lapatinib, HRG-β1 or antibodies as for proliferation assays. Following one or 24 hours incubation, cells were lysed using RIPA buffer (50 mM Tris, 150 mM NaCl, 0.5% sodium deoxycholate, 1% Triton X-100, 0.1% sodium dodecyl sulfate, 2 ug/mL aprotinin, 2 ug/mL leupeptin, 1 ug/mL pepstatin A, and 0.4 mg/mL pefabloc SC PLUS). Lysates were centrifuged for 20 minutes at 14,600 rpm at 4° C. and supernatants were collected. Protein concentrations in each lysate were determined using the BCA protein assay reagent (Pierce, catalog no. 23223). Total lysates were fractionated by SDS-PAGE and transferred onto polyvinylidene difluoride (PVDF) membranes (Millipore, catalog no. IPVH00010) or nitrocellulose membranes (Bio-Rad, catalog no 162.0145). Membranes were incubated with 5% bovine serum albumin in Tris-buffered saline with 0.1% Tween (TBST, pH 8.0) for 1 hour following transfer to block non-specific binding sites. Blocked membranes were incubated with primary antibodies overnight at 4° C. with agitation. Prior to incubation with the secondary antibodies conjugated to horseradish peroxidase, blots were washed three times (10 minutes/wash) with TB ST. Following incubation with secondary antibodies for 1 hour and washing, bound secondary antibody was detected using chemiluminescent detection regent (GE Healthcare, catalog no. RPN 2209/AF).

Example 6

Fluorescence Microscopy

SK-BR-3 cells incubated overnight at a density of 50,000 cells per dish were treated with 50 nM Ab6, Ab6tet, or TAb6 for 15 minutes at 37° C. and then either immediately washed and fixed or chased in medium at 37° C. for 45 minutes prior to washing and fixation. For fixation, cells were treated with 1.7% (w/v) paraformaldehyde for 10 minutes at 37° C. and then permeabilized with 0.05% (v/v) saponin for 10 minutes at room temperature in PBS. A pre-block with 4% BSA/PBS was carried out prior to staining with 2 µg/mL of polyclonal rabbit anti-LAMP-1 antibody (Abcam, catalog no. AB24170) and 12.5 µg/mL monoclonal mouse anti-EEA-1 (clone 14) from BD Bioscience (catalog no. 610456) for 30 minutes at room temperature. After blocking for 30 minutes with goat serum (Sigma-Aldrich, catalog no. G6767), bound primary antibodies were detected by incubating cells with the following secondary antibody conjugates for 25 minutes at room temperature: Alexa 555-labeled goat anti-human IgG (H+L) (Life Technologies, catalog no. A21433), Alexa 647-labeled goat anti-mouse IgG (H+L) (Life Technologies, catalog no. A21236) and Alexa 488-labeled goat anti-rabbit IgG (H+L) (Life Technologies, catalog no. A11034). Cells were washed twice with PBS between each incubation step and were stored at 4° C. in 1% BSA/PBS.

Images were acquired using a Zeiss Axiovert 200M inverted fluorescence microscope with a 63× Plan Apochromat objective as described previously. Data was processed using custom written software in MatLab (MIAtool/LABSoft; www.wardoberlab.com/software/miatool/).

Results

The inventors' study has led to several observations that are of relevance to targeting HER2 and HER3. First, we show that in the presence of heregulin, combination treatment with antibodies and lapatinib is necessary to achieve inhibition of signaling and growth. Under these conditions, a tetravalent HER3-specific antibody induces increased degradation of HER3 and has more potent anti-tumor effects relative to its bivalent counterpart. Importantly, when used in combination with lapatinib, the bispecific anti-HER2/HER3 antibody is a more effective inhibitor of heregulin-driven signaling and growth compared with anti-HER3 antibodies, tetravalent anti-HER3 antibodies or mixtures of individual antibodies specific for HER2 and HER3. The inventors' observations are consistent with a model in which the bispecific antibody recruits HER3 into HER2-HER3 heterodimers that are inactive in the presence of lapatinib.

Collectively, these studies provided support for the combined use of multimeric anti-growth factor receptor antibodies with small molecule TKI inhibitors for the therapy of cancer.

Antibodies Specific for HER2 and HER3 have Differential Effects on Signaling and Proliferation.

The anti-HER3 antibody, Ab6 (MM121, Schoeberl B, Faber A C, Li D, Liang M C, Crosby K, Onsum M, et al. An ErbB3 antibody, MM-121, is active in cancers with ligand-dependent activation. Cancer Res 2010; 70:2485-94), which competes with heregulin for binding to HER3 was used throughout the examples. To investigate whether a tetravalent anti-HER3 antibody is more effective than its bivalent counterpart in inhibiting cell growth and proliferation, the inventors fused the Ab6 single chain Fv (scFv) to the CH3 domains of Ab6 via a Gly-Ser-Ser linker. In addition, a bispecific trastuzumab (anti-HER2)-Ab6 antibody (TAb6) was generated by fusing scFv fragments corresponding to Ab6 to the CH3 domain of trastuzumab using an analogous design (FIG. 1). All antibodies were expressed in transfected CHO cells.

Figure 2:
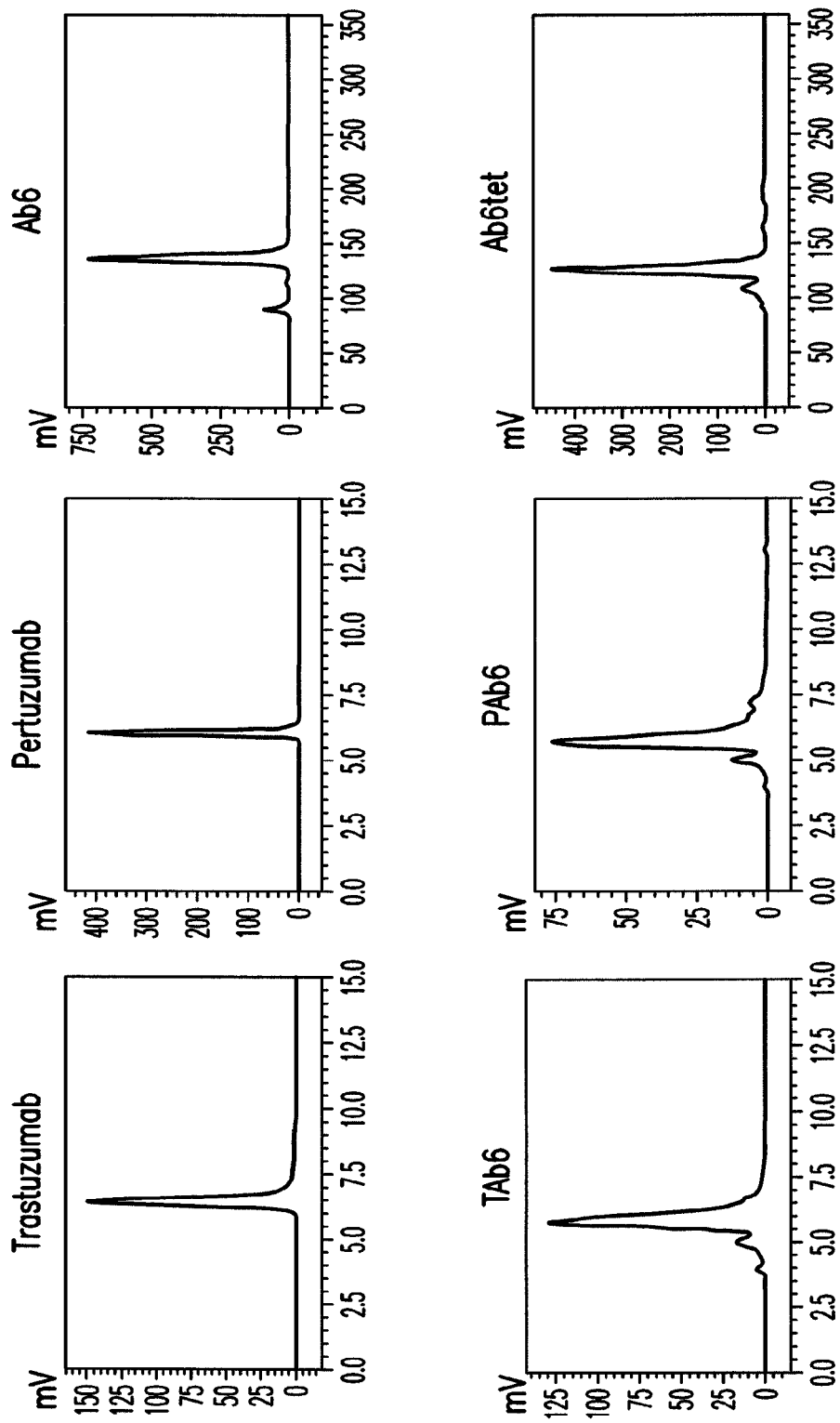
FIG. 2 Shows analysis of trastuzumab, pertuzumab, Ab6, bispecific trastuzumab with anti-HERS Ab6 scFv (TAb6), bispecific pertuzumab with anti-HERS Ab6 scFv (PAb6), and tetrameric anti-HERS (Ab6tet) using HPLC and size exclusion chromatography. Trastuzumab, pertuzumab, TAb6 and PAb6 were analysed using a Yana 3U SEC-3000 column, where as a Hiload 16/600 Superdex 200 pg column was used for Ab6 and Ab6tet. The major peak runs at the expected size for either an antibody homodimer (150 kDa) or bispecific homodimer (200 kDa).
Figure 3:
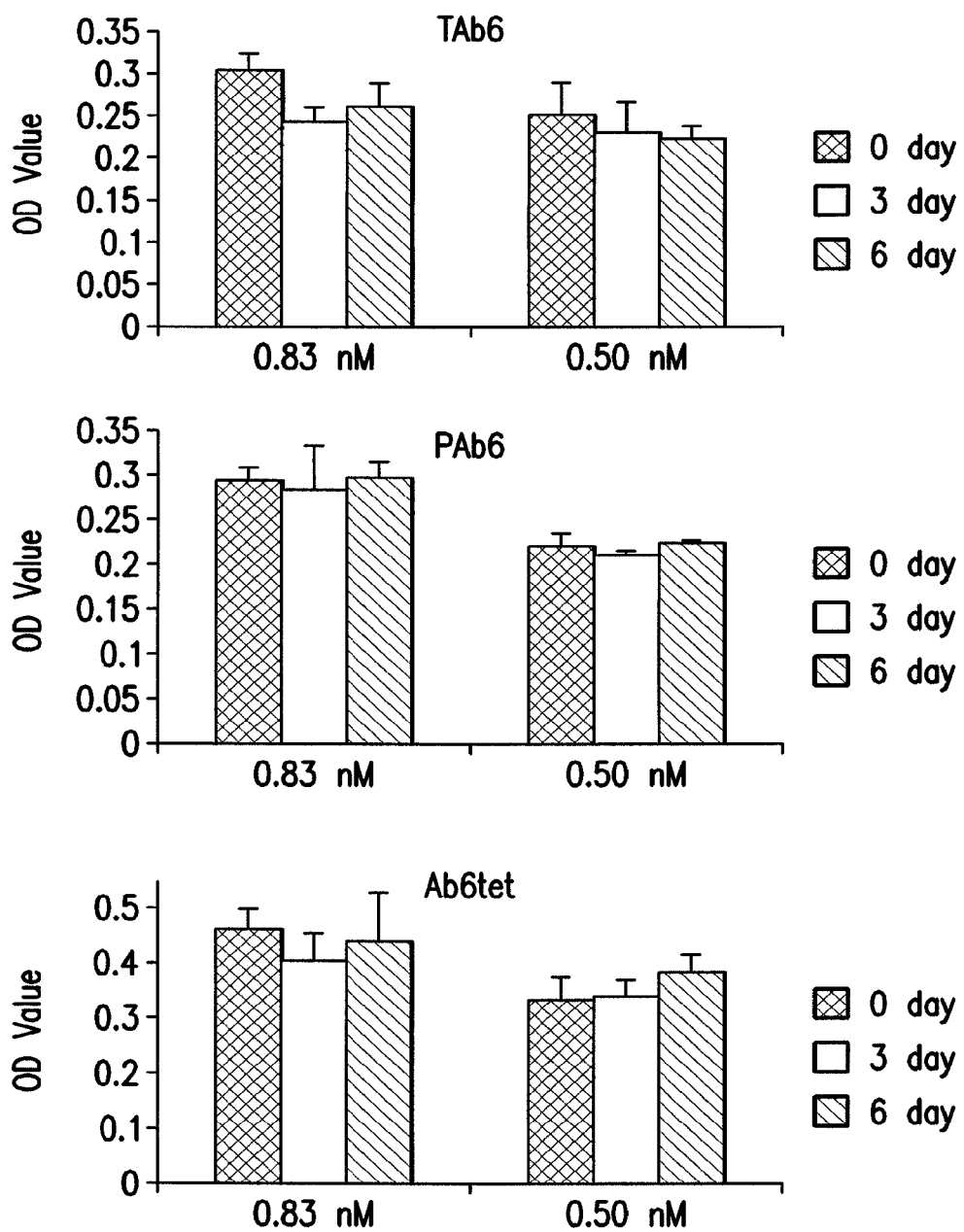
FIG. 3 Shows serum stability analyses of the bispecific trastuzumab with anti-HER3 Ab6 scFv (TAb6), bispecific pertuzumab with anti-HER3 scFv (PAb6), and tetrameric anti-HER3 (Ab6tet). Antibodies were incubated in mouse serum for 0, 3, or 6 days at 37° C., diluted into PBS to concentrations of 0.83, 0.50 nM, and analyzed by sandwich ELISA. Differences were not significant for comparisons of 0 and 6 day samples (p value>0.05; Student's t test).

The expression yields of the bispecific antibodies were 4.5 mg/L, 2.5 mg/L and 8 mg/L for Ab6tet, PAb6 and TAb6, respectively. Size exclusion and serum stability analyses of the bispecific proteins are presented in the FIGS. 2 and 3. For comparative purposes, size exclusion studies of Ab6, trastuzumab and pertuzumab are shown (FIG. 2). Ab6 and the bispecific antibodies also bound to immobilized, recombinant Fc-HER2 (TAb6, PAb6) or HER3 (Ab6, Ab6tet, TAb6, PAb6) in surface plasmon resonance experiments (BIAcore; data not shown). The in vivo half-lives ($\beta$-phase) of Ab6tet and TAb6 were also determined in BALB/c SCID mice and were 228±14 (n=4 mice) and 215±11 (n=5 mice) hours, respectively.

Figure 4A:
FIG. 4A, 4B: Effects of antibodies specific for HER2 and/or HER3 on HER2-overexpressing breast cancer cells.

The inventors initially assessed the effect of targeting HER3 and HER2/HER3 with several different antibody formats in the absence of the HER3 ligand, heregulin. For comparative purposes the inventors also included the anti-HER2 antibodies, trastuzumab and pertuzumab, which bind to domain IV and the dimerization arm (domain II), respectively, of HER2. The anti-HER3 antibody, Ab6, and its tetrameric form, Ab6tet, reduced proliferation in the HER2-overexpressing cancer cell lines, SK-BR-3 and HCC1419 (FIG. 4A). Although Ab6 and Ab6tet treatment resulted in a trend towards reduced proliferation in BT-474 cells, the effects were not significant. By contrast with SK-BR-3 and HCC1419 cells, BT-474 cells express a gain of function variant of PI3K which could account for the reduced efficacy of anti-HER3 antibodies. Consistent with the observations of others, trastuzumab has higher anti-proliferative activity on ligand-independent growth of SK-BR-3 and BT-474 cells relative to pertuzumab (FIG. 4A).

Although combinations of anti-HER2 and anti-HER3 antibodies (Ab6 combined with trastuzumab or pertuzumab) had anti-proliferative activities, exposure of cells to the bispecific, TAb6, comprising trastuzumab plus Ab6, resulted in increased proliferation (FIG. 4A). Further, a bispecific antibody comprising Ab6 and pertuzumab (PAb6) induced proliferation (FIG. 4A). The effects of both PAb6 and TAb6, which bind to different sites of HER2, indicate that proximity of HER2 and HER3 is sufficient for proliferative signaling, rather than a need for the receptors to dimerize in a specific configuration. This proximity model is also consistent with the observation that exposure of cells to a mixture of trastuzumab or pertuzumab and Ab6, which would not be expected to drive formation of HER2-HER3 heterodimers, results in reduced proliferation (FIG. 4A).

Figure 4B:
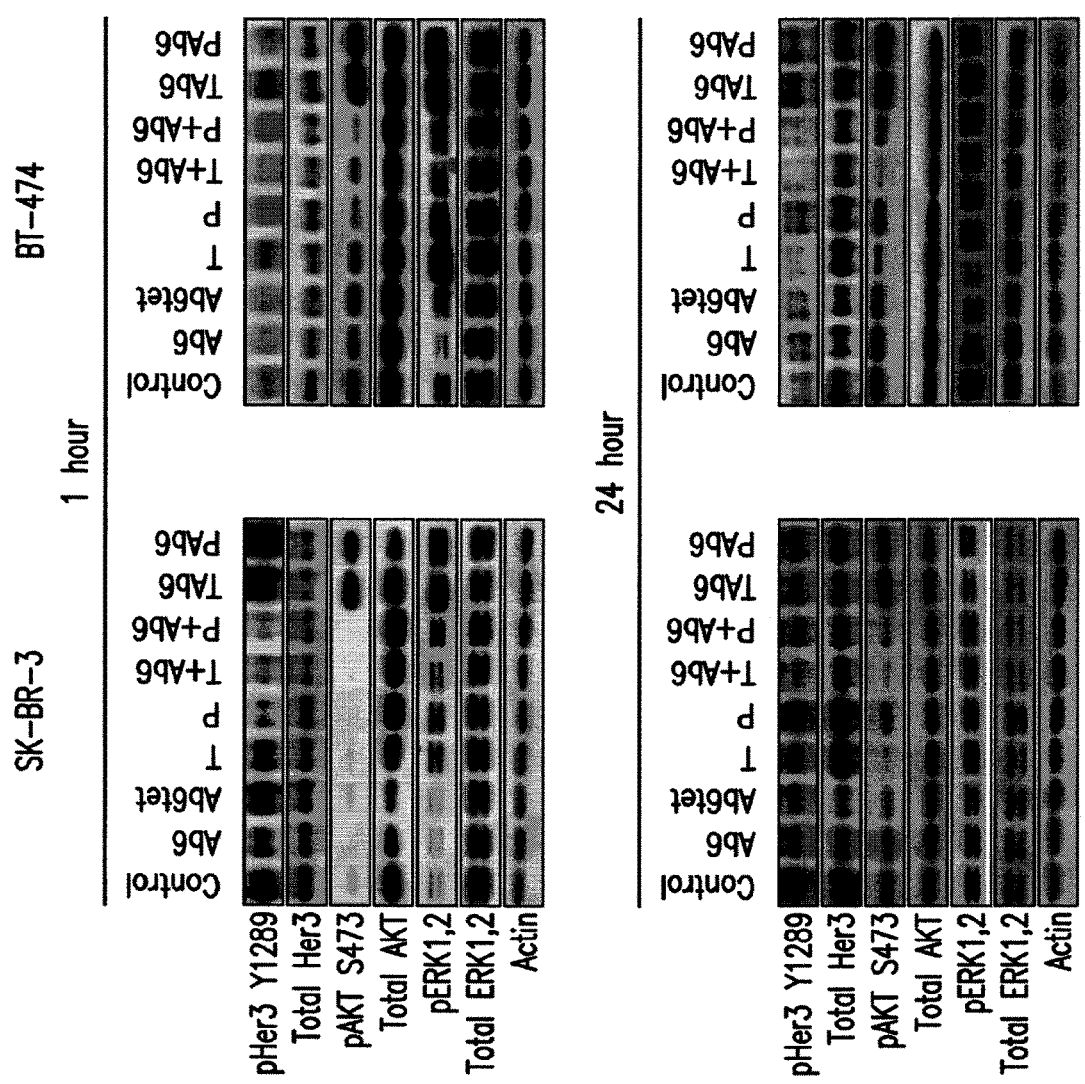
Figure 5:
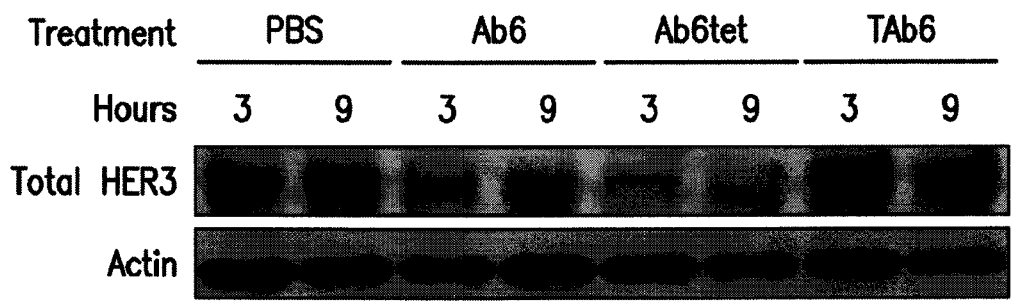
FIG. 5: The multivalent anti-HER3 antibody, Ab6tet, induces higher levels of HER3 degradation compared with the bivalent counterpart, Ab6. SK-BR-3 cells were treated with 50 nM anti-HER3 antibody (Ab6), Ab6tet, bispecific trastuzumab with anti-HER3 Ab6 scFv (TAb6), or PBS vehicle for 3 or 9 hours. Cell lysates were analyzed for total HER3 using immunoblotting.

Analyses of the effects of the antibodies on the phosphorylation of HER3, Akt and Erk, demonstrated that the anti-proliferative effects are associated with decreased pAkt levels in SK-BR-3 and BT-474 cells (FIG. 4B). Although pErk levels were lower following treatment of cells for one hour with Ab6, Ab6tet, or Ab6 combined with anti-HER2 antibodies than for cells treated with trastuzumab, pertuzumab, TAb6 or PAb6, these differences were not sustained at the 24 hour time point (FIG. 4B). Exposure of SK-BR-3 or BT-474 cells to TAb6 or PAb6 resulted in increased pAkt (S473) levels that persisted for at least 24 hours, consistent with the pro-proliferative effects of these bispecific antibodies. By contrast, the levels of pAkt at 24 hours were decreased in cells treated with any of the other antibodies or antibody combinations (FIG. 4B). In addition, total HER3 levels at 24 hours were reduced by treatment with anti-HER3 antibodies, whereas exposure of cells to the bispecific antibodies, TAb6 and PAb6, resulted in less HER3 degradation (FIGS. 4B, 5). Reduced HER3 degradation following TAb6 or PAb6 treatment is consistent with the inhibitory effects of HER2 expression on the internalization of EGFR or HER3 The increased degradation induced by Ab6tet relative to Ab6 was more marked for SK-BR-3 than BT-474 cells (FIG. 4B).

Figure 6:
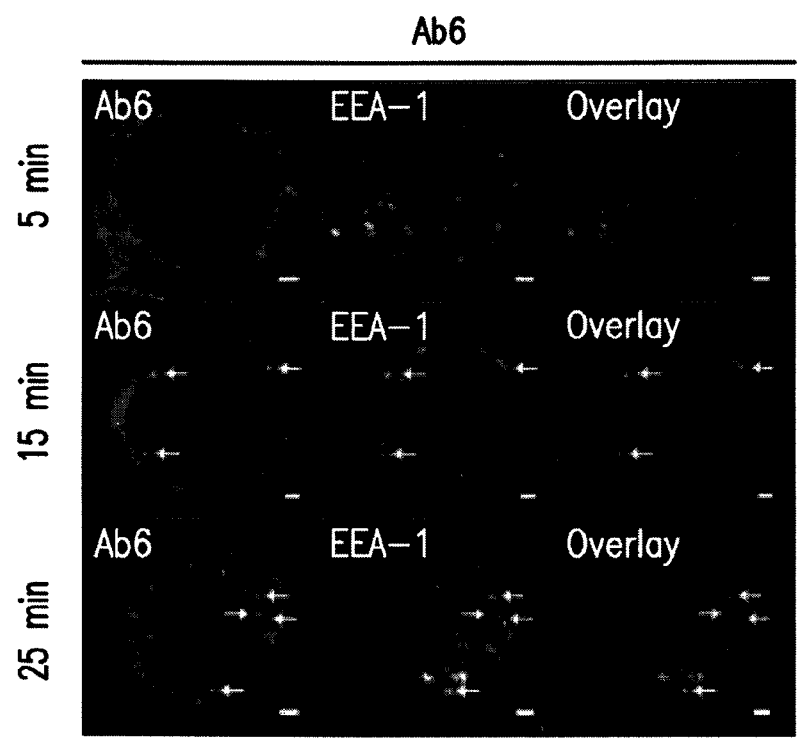
FIG. 6: Ab6tet internalizes into SK-BR-3 cells more rapidly than Ab6. Cells were pulsed with 50 nM anti-HER3 (Ab6), tetrameric anti-HER3 (Ab6tet) or bispecific trastuzumab with anti-HER3 Ab6 scFv (TAb6) for 5 minutes at 37° C., chased for 0, 10 or 20 minutes, fixed, permeabilized and stained with anti-EEA-1 antibody. The combined pulse plus chase times are indicated on the left margin. Anti-HER3 or HER2/HER3 antibodies were detected with Alexa 555-labeled secondary antibody (pseudocolored red in overlay) and anti-EEA-1 antibody with Alexa 647-labeled secondary antibody (pseudocolored green in overlay). Yellow arrows in the images for Ab6tet-treated cells indicate examples of internalized Ab6tet that is associated with EEA-1 positive endosomes. Scale bars=2 μm.
Figure 6:
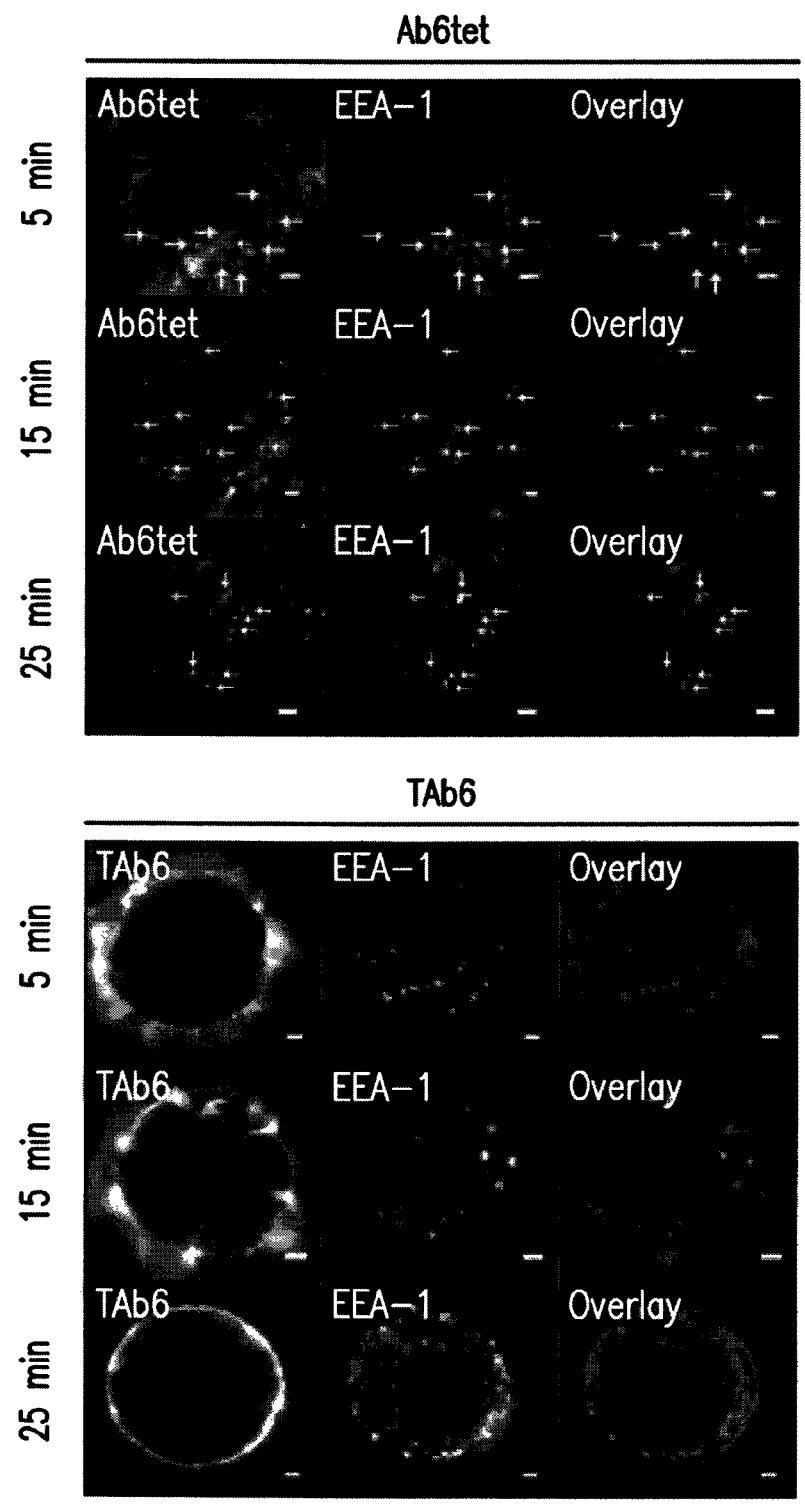
Figure 7:
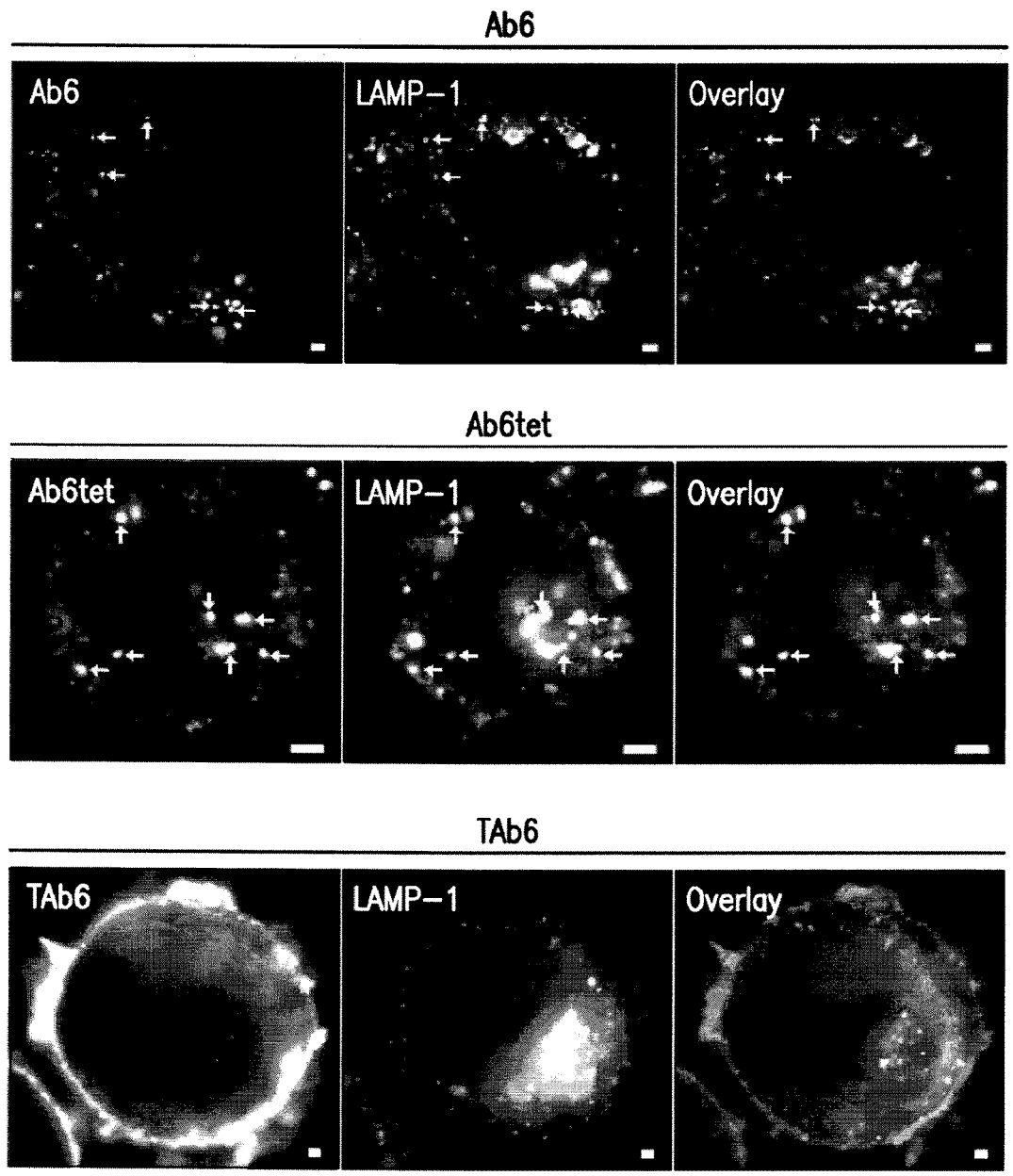
FIG. 7: The bivalent anti-HER3 antibody, Ab6, and its multivalent counterpart, Ab6tet, traffic into LAMP-1 positive endosomal structures within one hour of treatment. SK-BR-3 cells were treated with 50 nM Ab6, Ab6tet, or bispecific trastuzumab with anti-HER3 scFv Ab6 (TAb6) for 15 minutes at 37° C. and chased in medium for 45 minutes at 37° C. Cells were fixed, permeabilized and stained for LAMP-1. Anti-HER3 or HER2/HER3 antibodies were detected with Alexa 555-labeled secondary antibody (pseudocolored red in overlay) and anti-LAMP-1 antibody with Alexa 488-labeled secondary antibody (pseudocolored green in overlay). Examples of co-localization of antibody and LAMP-1+ compartments are indicated by yellow arrows. Scale bars=2 μm.

Microscopy analyses were used to further investigate the intracellular trafficking pathways taken by Ab6, Ab6tet and TAb6 (FIG. 6). These studies demonstrate that Ab6tet is internalized into EEA-1 positive early endosomes more rapidly than Ab6, and enters these compartments within 5 minutes of treatment. Following 15 minutes of treatment, both Ab6 and Ab6tet are internalized into early endosomes, although the levels of Ab6 remaining on the plasma membrane are greater than for Ab6tet (FIG. 6). By contrast, the majority of TAb6 is present on the plasma membrane following 5-60 minutes of treatment (FIGS. 6, 7). Within one hour of treatment, Ab6 and Ab6tet is present in LAMP-1+ lysosomes (FIG. 7). Multivalent antibody binding to HER3 therefore enhances the rate of HER3 internalization into the endolysosomal pathway, consistent with the increased degradation of HER3 in the presence of Ab6tet relative to Ab6.

Targeting HER2/HER3 with Antibodies is Ineffective in the Presence of Heregulin.

Figure 8A:
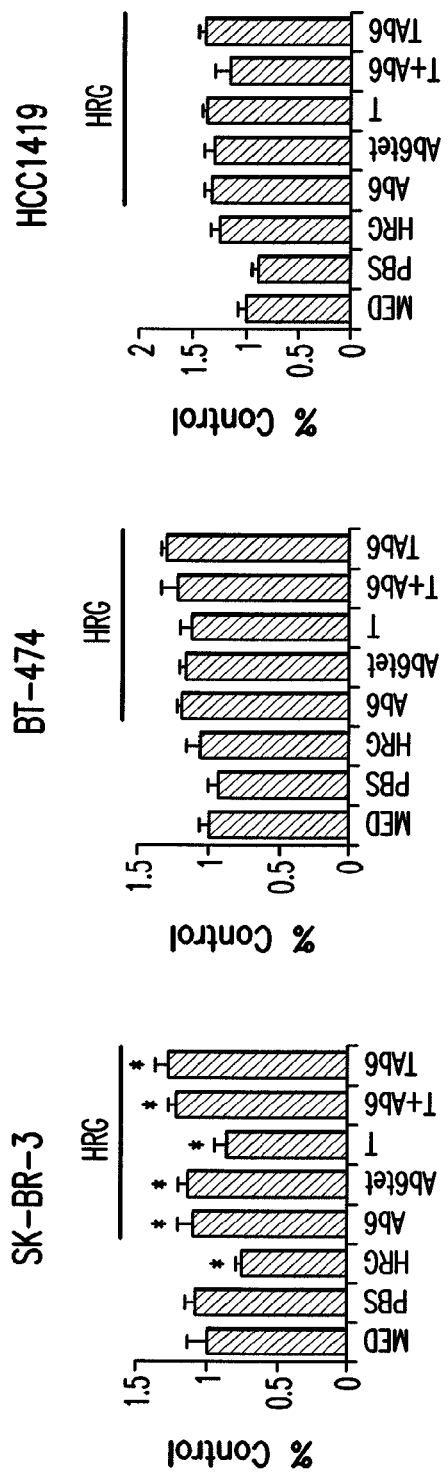
FIG. 8A, 8B: Antibodies specific for HER2 and/or HER3 have reduced efficacy in inhibiting proliferation and PI3K/
Figure 8B:
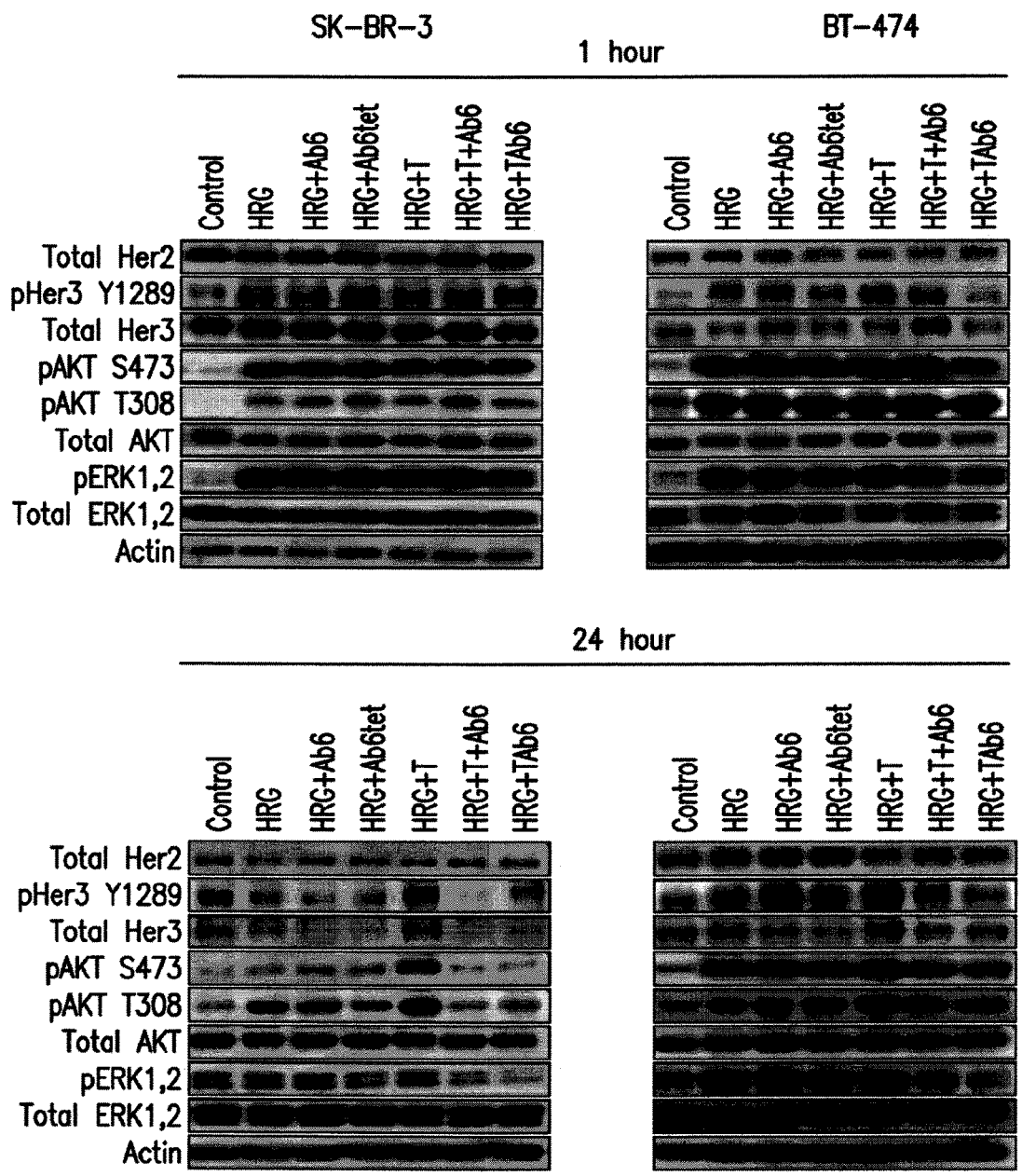

Heregulin is frequently present in tumors due to autocrine and/or paracrine production, motivating an investigation of the effects of the antibodies on tumor cell growth in the presence of this HER3 ligand. HCC1419 cells showed increased proliferation in the presence of heregulin, whereas reduced proliferation was observed for SK-BR-3 cells (FIG. 8A). Although BT-474 cells showed a trend towards heregulin-stimulated proliferation, differences between vehicle- and heregulin-treated cells were not always significant. Reduced proliferation of SK-BR-3 cells in response to heregulin has been described previously. Heregulin exposure ablated the inhibitory effects of Ab6, Ab6tet, trastuzumab or trastuzumab plus Ab6 on ligand-independent proliferation of BT-474 or HCC1419 cells (FIGS. 4A, 8A). Slightly higher proliferation of HCC1419 cells were observed following TAb6 relative to trastuzumab plus Ab6 treatment, but differences for these two treatments were not significant for SK-BR-3 and BT-474 cells. The reduced efficacy of the antibodies in the presence of heregulin was accompanied by either no change (SK-BR-3 cells with trastuzumab and TAb6 24 hours following treatment and BT-474 cells with all treatments), or a reduction (SK-BR-3 cells with Ab6, Ab6tet, or a mixture of trastuzumab plus Ab6 at 24 hours) in pAkt levels. Collectively, the data indicate that antibody targeting of HER2 and HER3 has limited efficacy in the presence of intratumoral HER3 ligands.

Figure 9A:
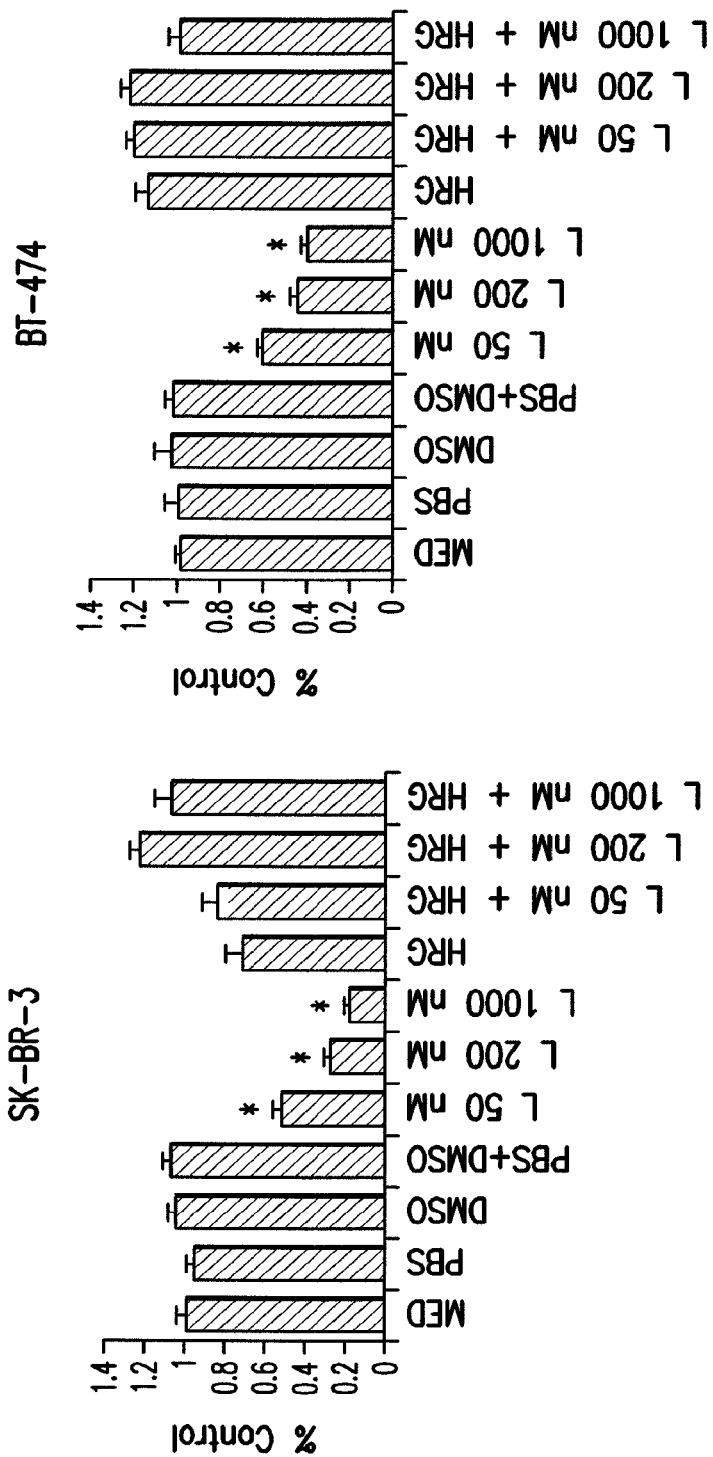
FIG. 9A, 9B: Heregulin treatment reverses the anti-proliferative effects of lapatinib in HER2 overexpressing cell lines.
Figure 9B:
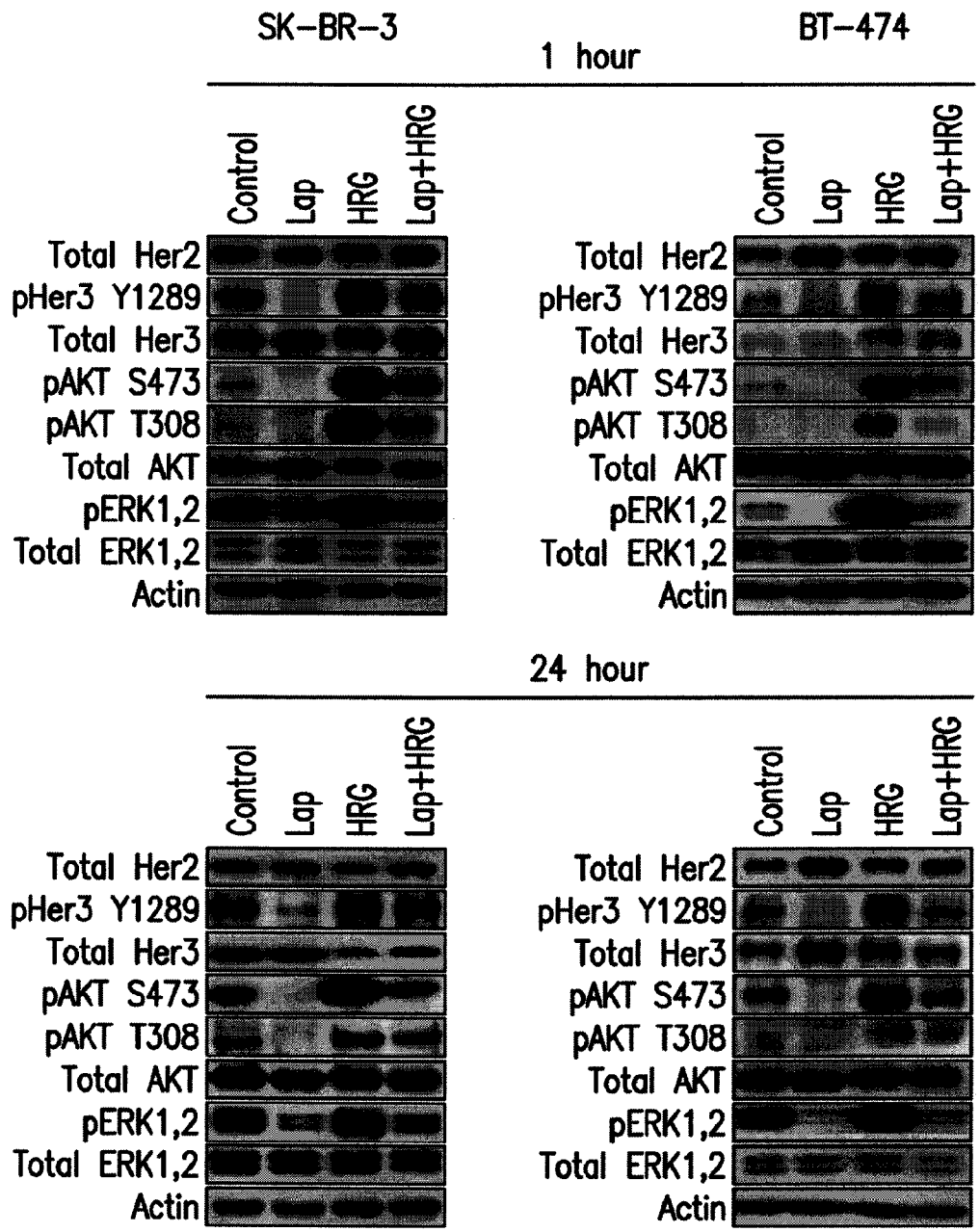
Figure 10:
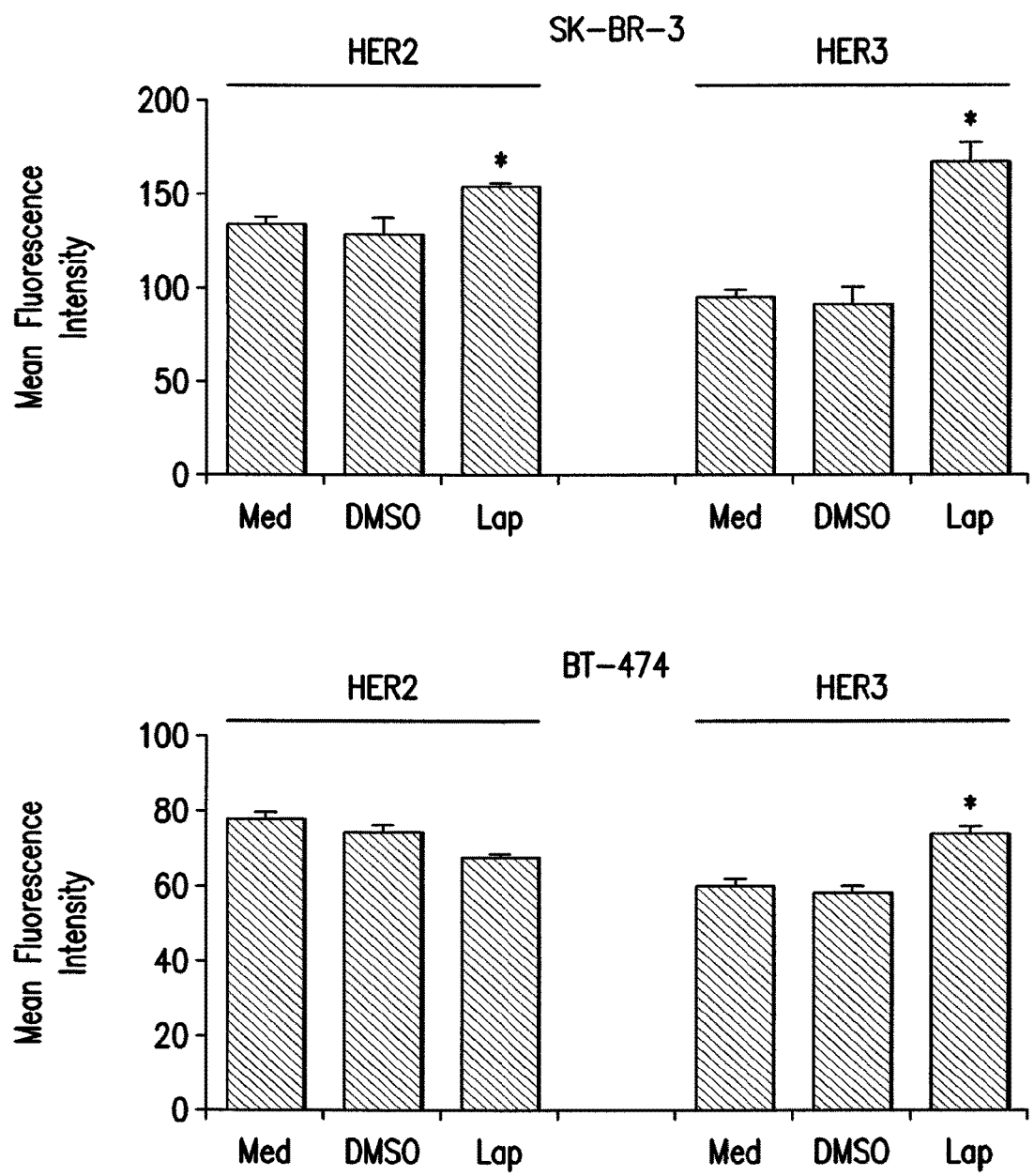
FIG. 10: Lapatinib treatment induces upregulation of HER2 and HER3 (SK-BR-3) or HER3 (BT-474) levels on the plasma membrane of breast cancer cells. Cells were treated with 1 μM lapatinib (Lap), medium (Med) or vehicle control (DMSO) for 24 hours. Cell surface HER2 or HER3 was detected by incubation with 50 nM Alexa 488-labeled trastuzumab or Alexa 647-labeled Ab6 followed by flow cytometric analyses. Data shown represent means of mean fluorescence intensities±standard deviation of triplicate samples following subtraction of background fluorescence intensities. * indicates statistically significant differences between lapatinib and DMSO (vehicle) treated cells (p<0.005; Student's t test). Data shown are representative of at least two independent experiments.

Lapatinib Combined with Antibodies Specific for HER2/HER3 Overcomes Heregulin-Mediated Resistance The induction of proliferative signaling by HER2-HER3 dimerization 'forced' by TAb6 treatment suggested that the combination of this bispecific antibody with the small molecule inhibitor of HER2 (and EGFR) kinase activity, lapatinib, might stabilize HER2-HER3 heterodimers in an inactive state. Further, the inventors hypothesized that such complexes would preclude the interaction of HER3 with signaling competent partners. Lapatinib treatment is known to result in upregulation of HER2 and HER3 levels on the plasma membrane, and the inventors confirmed these observations under the conditions of the inventors assay (except that HER2 was not upregulated on BT-474 cells; FIG. 10). Treatment of SK-BR-3 and BT-474 cells with lapatinib at doses ranging from 50 nM-1 µM resulted in inhibition of proliferation (FIG. 9A). However, this growth inhibition was ablated by exposure of cells to heregulin (FIG. 9A). Although lapatinib treatment alone resulted in potent inhibition of HER3, Akt and Erk phosphorylation, this was partially reversed by incubation of cells with lapatinib plus heregulin (FIG. 9B).

Figure 11A:
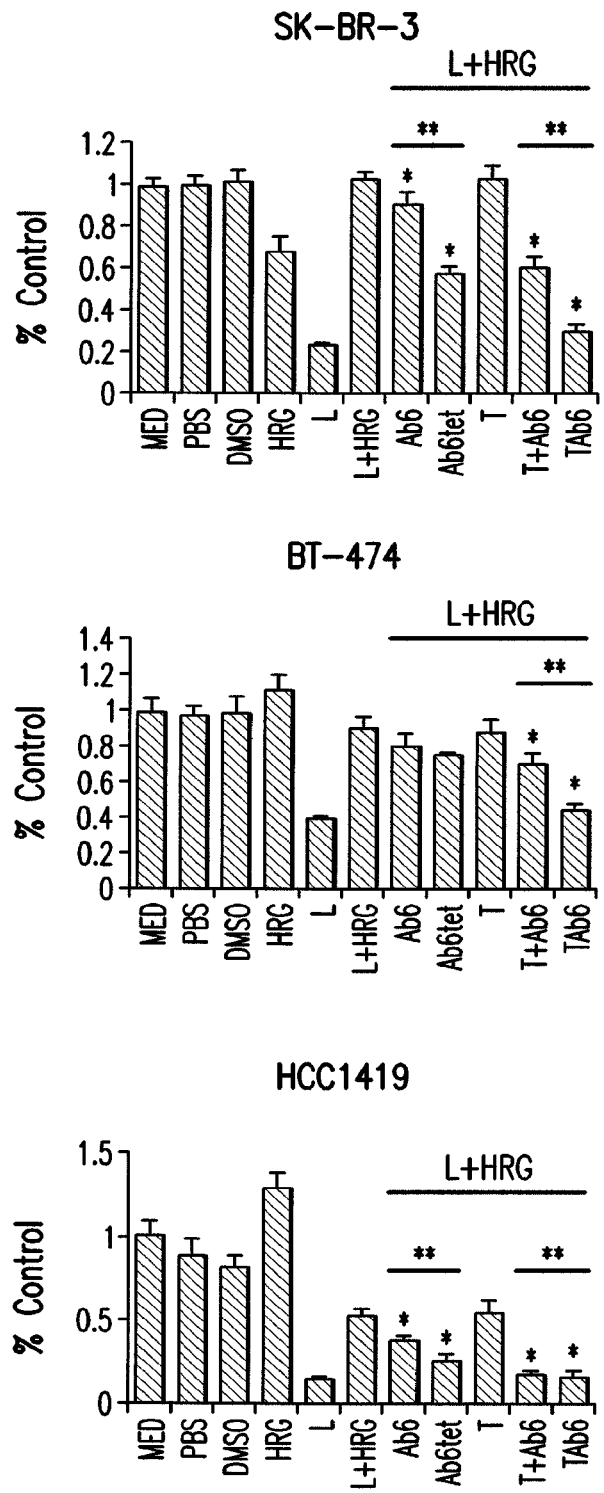
FIG. 11A, 11B: The bispecific anti-HER2/HER3 antibody, TAb6, has the highest activity in reducing cell proliferation and PI3K/pAkt signaling in the presence of heregulin and lapatinib.
Figure 12:
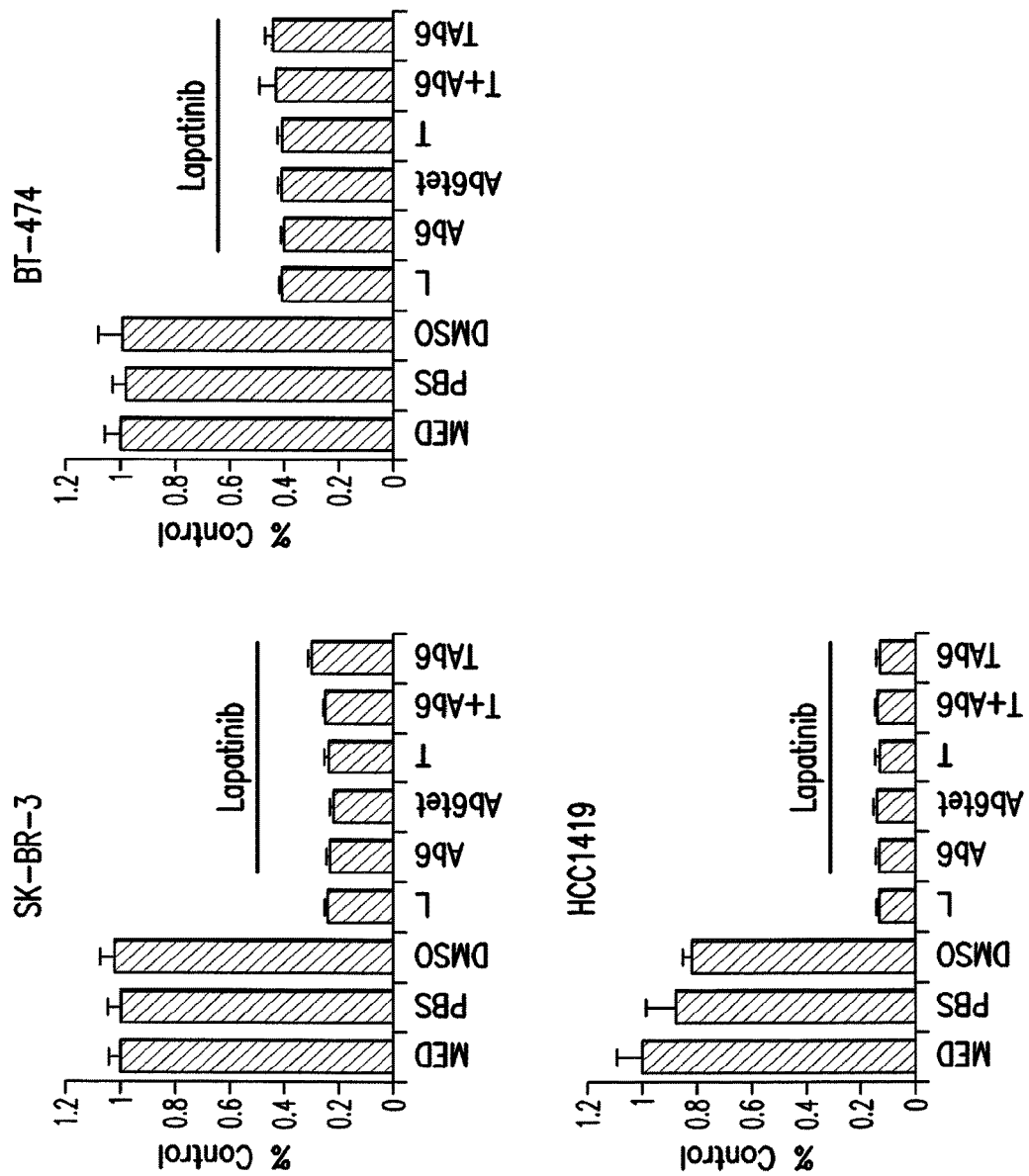
FIG. 12: Antibodies specific for HER2 and/or HER3 do not increase the anti-proliferative effect of lapatinib. SK-BR-3, BT-474, and HCC1419 cells were treated with 1 μM lapatinib (L) alone or lapatinib in combination with 50 nM anti-HER3 (Ab6), tetrameric anti-HER3 (Ab6tet), trastuzumab (T), trastuzumab and Ab6 (T+Ab6) or bispecific trastuzumab with anti-HER3 Ab6 scFv (TAb6) for 5 days. Proliferative responses were assessed using the MTS reagent and were normalized against the proliferation of cells incubated in medium (Med) only. Data shown are means of triplicates±standard deviation and are representative of at least two independent experiments.

The observation that lapatinib alone has limited efficacy in blocking cell proliferation in the presence of heregulin prompted us to investigate the effect of combination treatment of heregulin-exposed SK-BR-3, BT-474 and HCC1419 cells with lapatinib and HER3-targeting antibodies. Addition of Ab6 or Ab6tet to lapatinib resulted in anti-proliferative effects compared with the effects of lapatinib alone (FIG. 11A). In addition, for SK-BR-3 and HCC1419 cells, Ab6tet was more effective than Ab6 (FIG. 11A). Consistent with the inability of trastuzumab to inhibit ligand-dependent HER2-HER3 signaling, this HER2-specific antibody did not reduce proliferation in the presence of heregulin and lapatinib. By contrast, of the antibodies/bispecifics tested, the anti-HER2/HER3 bispecific, TAb6, was the most potent of the antibodies tested in combination with lapatinib in reducing proliferation of heregulin-treated cells (FIG. 11A) Importantly, this bispecific also had increased anti-proliferative effects relative to a mixture of trastuzumab and Ab6 (FIG. 11A). In the absence of heregulin, none of the antibodies further reduced the anti-proliferative activity of lapatinib (FIG. 12).

Figure 11B:
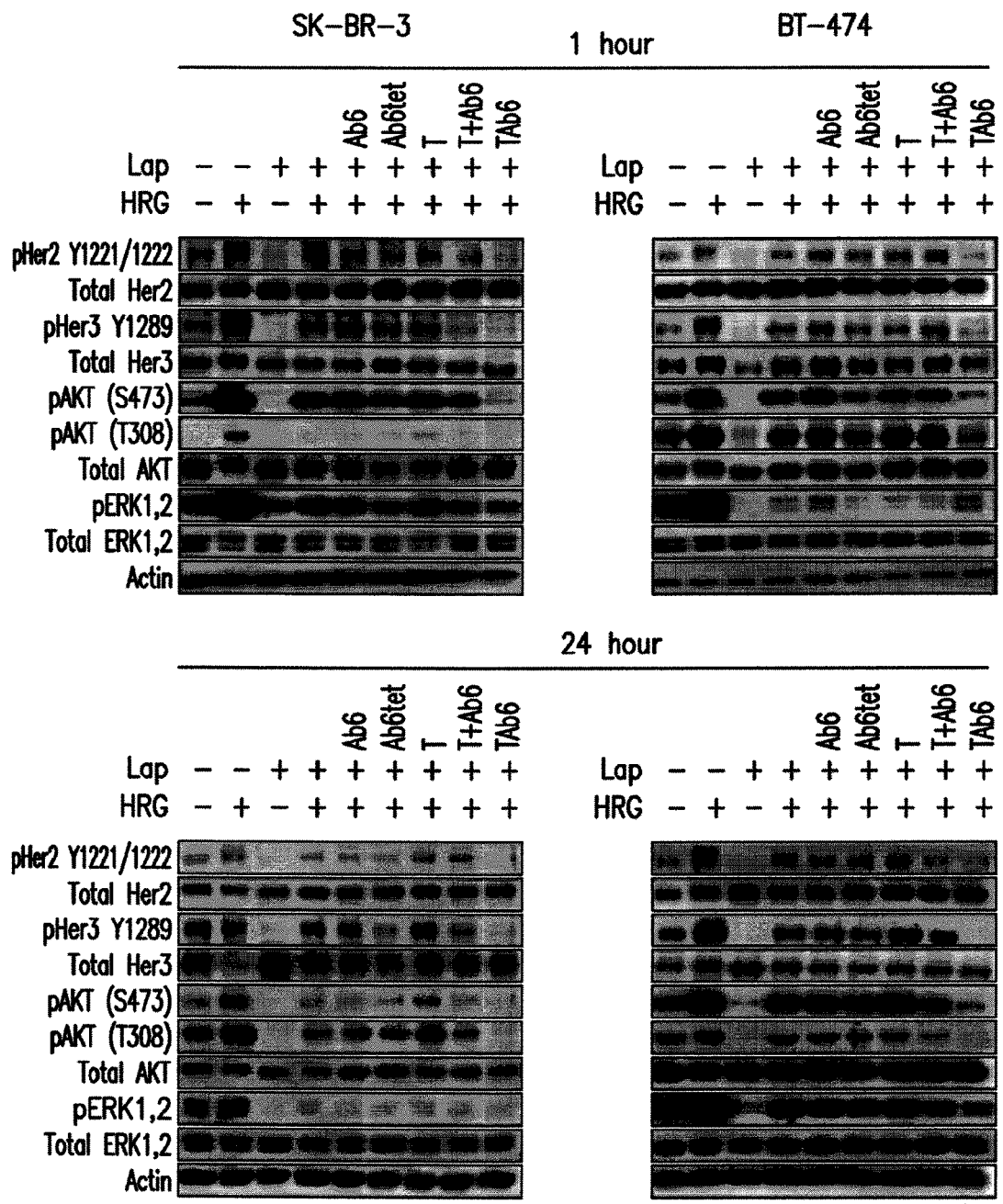
Figure 13:
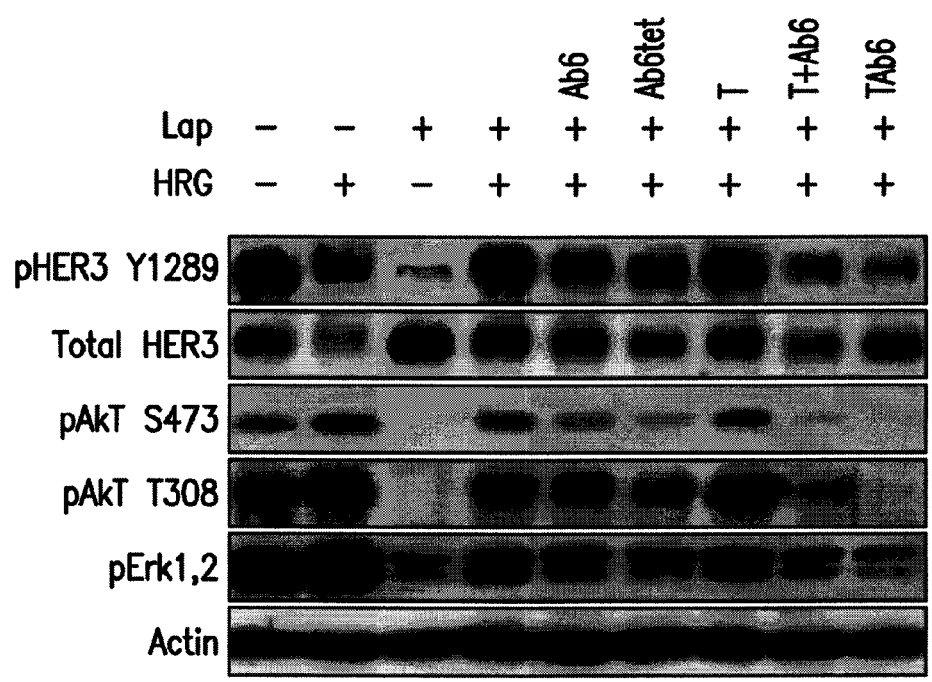
FIG. 13: The bispecific antibody comprising trastuzumab with anti-HER3 Ab6 scFv (TAb6) has the highest activity in reducing PI3K/Akt signaling in HCC1419 cells in the presence of heregulin and lapatinib. Cells were treated for 24 hours with 1 μM lapatinib (Lap), 6.25 nM heregulin (HRG) and 50 nM anti-HER3 (Ab6), tetrameric anti-HER3 (Ab6tet), trastuzumab (T), trastuzumab and Ab6 (T+Ab6) or TAb6 as indicated. Cell lysates were analyzed by immunoblotting.
Figure 14:
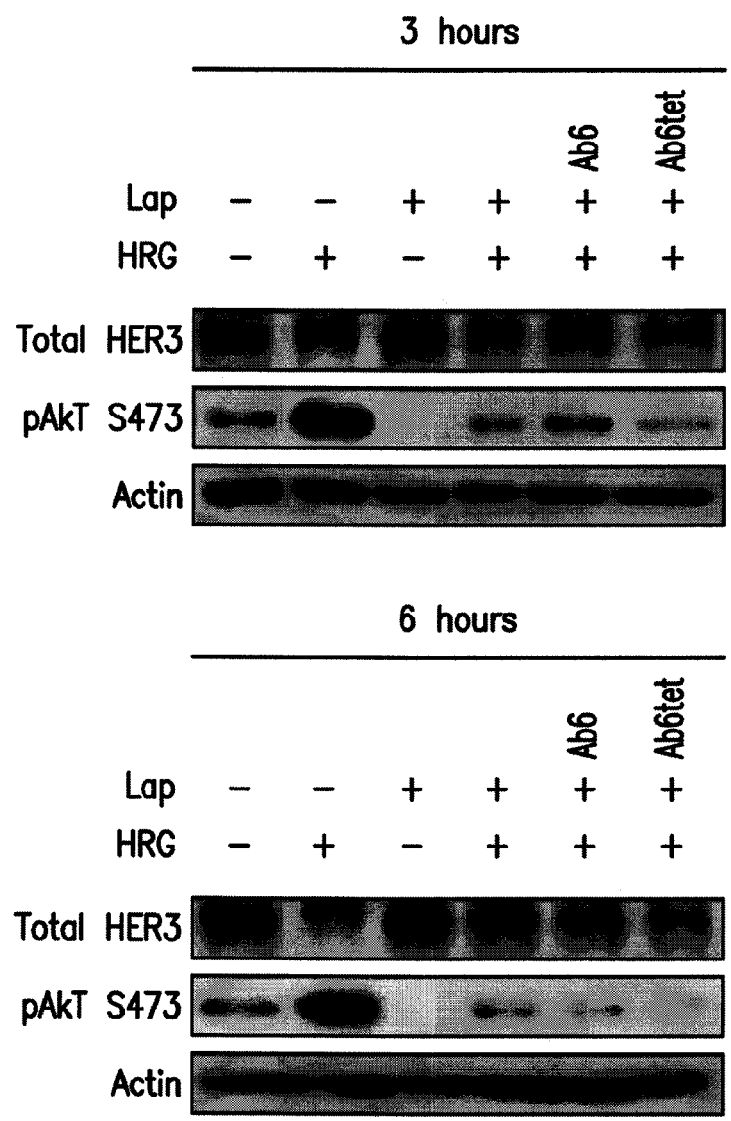
FIG. 14: The multivalent anti-HER3 antibody, Ab6tet, induces higher levels of HER3 degradation compared with the bivalent counterpart, Ab6, in the presence of heregulin (HRG) and lapatinib (Lap). SK-BR-3 cells were treated as indicated with combinations of 1 μM lapatinib, 6.25 nM heregulin, 50 nM anti-HER3 (Ab6) or tetrameric anti-HER3 (Ab6tet) for 3 or 6 hours. Cell lysates were analyzed for total HER3 and pAkt (S473) by immunoblotting.

In the presence of lapatinib and heregulin, Ab6tet, trastuzumab plus Ab6 or TAb6 treatment resulted in lower levels of pHER3, pErk and pAkt (S473, T308) for SK-BR-3 and HCC1419 cells (FIGS. 11B, 13). The improved activity of Ab6tet compared with Ab6 in SK-BR-3 and HCC1419 cells is consistent with the increased degradation of HER3 in the presence of the tetrameric antibody (FIGS. 11B, 13, 14). TAb6 was the most potent antibody in reducing downstream signaling in SK-BR-3, BT-474 and HCC1419 cells, and was more inhibitory than mixtures of trastuzumab and Ab6 (FIG. 11B). Further, TAb6 was the only antibody in combination with lapatinib that reduced heregulin-induced pAkt and pErk in BT-474 cells. Collectively, the data indicate that in the presence of lapatinib the bispecific antibody, TAb6, is the most potent inhibitor of ligand-induced activation.

The limitations of targeting individual components of the HER3/PI3K/Akt signaling axis, including the activity of the preferred dimerization partner HER2, is well documented. Several factors contribute to the poor efficacy of this approach: first, antibodies specific for HER2 and HER3 have reduced activity in inhibiting proliferation and signaling in the presence of the HER3 ligand heregulin, which is expressed in multiple tumor types. Second, the use of small molecule TKIs such as lapatinib or gefitinib results in compensatory HER2 and HER3 upregulation and signaling through either incomplete blockade of HER2 kinase activity or HER3 association with other signaling competent partners. Third, these compensatory effects are exacerbated by the presence of heregulin. Consequently, TKIs such as lapatinib are ineffective as single agents in inhibiting breast tumor cell proliferation, indicating a need for the development of combination therapies. An analysis was conducted of the efficacy of two HER3-focused strategies directed toward reducing breast cancer cell signaling and proliferation. These approaches also have broader relevance to the targeting of other cell surface receptors, and involve the use of distinct antibody designs to recruit HER3 into kinase-inhibited HER2-HER3 complexes or induce HER3 degradation. It was demonstrated that the recruitment of HER3 into lapatinib-inactivated HER2-HER3 complexes by a bispecific anti-HER2/HER3 antibody (TAb6, comprising trastuzumab and an anti-HER3 scFv) is efficacious in both ablating PI3K/Akt signaling and reducing tumor cell proliferation in the presence of heregulin Importantly, and of direct relevance to therapy, the bispecific antibody is a more potent inhibitor of signaling and growth than either HER2- or HER3-specific antibodies alone or a mixture of antibodies of both specificities. In a second approach, we have compared the effect on tumor cell signaling and growth of a multivalent anti-HER3 antibody (Ab6tet) that is designed to enhance HER3 degradation with its bivalent counterpart, Ab6. In the presence of heregulin and lapatinib, Ab6tet has higher activity. By comparison with bivalent Ab6, this multivalent construct induces more rapid HER3 internalization into early endosomes. By contrast, the bispecific TAb6 induces less HER3 degradation than either Ab6 or Ab6tet, and yet is more effective in reducing cell signaling and proliferation. This indicates that the internalization resistance and/or recycling behavior of HER2 has a dominant effect on HER3 in the forced HER2-HER3 heterodimers. Further, the internalization resistance is consistent with earlier studies in which endocytic uptake of EGFR or HER3 is reduced by dimerization with HER2 Importantly, our data indicate that the locking of HER3 into inactive HER2-HER3 complexes, even if they remain on the plasma membrane, is a more effective strategy for the ablation of heregulin-mediated signaling than induction of increased HER3 degradation. In addition, analogous approaches could be extended to the design of bispecifics for the recruitment of HER3 into heterodimers with other partners for tumors that do not overexpress HER2.

The question arises as to why the anti-HER3 antibody, which competes for heregulin binding, is not as effective either alone or in combination with trastuzumab as the bispecific antibody, TAb6, in reducing HER3-PI3K signaling. In addition to locking HER3 into dimers, TAb6 would be expected to enhance the avidity of binding of Ab6 to HER3 through bridging of trastuzumab-HER2 complexes. The trastuzumab-HER2 interaction is of very high affinity (100 pM, Carter P, Presta L, Gorman C M, Ridgway J B, Henner D, Wong W L, et al. Humanization of an anti-p185HER2 antibody for human cancer therapy. *Proc Natl Acad Sci USA* 1992; 89:4285-9), and this, combined with high HER2 expression levels on the cell surface, should increase avidity effects. Further, although Ab6tet is expected to bind with increased avidity over Ab6 through increased valency, the Ab6-HER3 interaction is of much lower affinity (0.8 nM, Schoeberl B, Pace E A, Fitzgerald J B, Harms B D, Xu L, Nie L, et al. Therapeutically targeting ErbB3: a key node in ligand-induced activation of the ErbB receptor-PI3K axis. *Sci Signal* 2009; 2:ra31). Thus, the improved efficacy of Ab6tet relative to Ab6 could be due to both increased degradation of HER3 and higher avidity binding, but the avidity enhancement resulting from multivalent binding would be lower than that for TAb6.

The use of bispecific antibodies of different formats is an active area in the development of cancer therapeutics (Reichert J M, Dhimolea E. The future of antibodies as cancer drugs. *Drug Discov Today* 2012; 17:954-63). For example, strategies to target both HER2 and HER3 using several different bispecific antibody formats or mixtures of antibodies have been described. Of relevance to the use of bispecifics, however, the inventors observed that in the absence of lapatinib (and heregulin), exposure of SK-BR-3, BT-474 or HCC1419 cells to bispecific antibodies comprising either trastuzumab or pertuzumab and the anti-HER3 scFv, Ab6 (TAb6 or PAb6, respectively), results in increased PI3K/Akt signaling and proliferation. The observation that bispecifics containing either trastuzumab (TAb6) or pertuzumab (PAb6) are both active in inducing HER3 phosphorylation and PI3K/Akt signaling suggests that proximity rather than a specific configuration of HER2 and HER3 is sufficient for HER3 transphosphorylation. This is consistent with our observation that bispecific HER2/HER3 specific antibodies can sequester HER3 into HER2-HER3 heterodimers that, if inhibited by HER2-specific TKIs, effectively silence HER3.

The inventors have also characterized the impact of using antibodies of different designs on intracellular trafficking. The increased internalization and trafficking to lysosomes induced by using a multivalent anti-HER3 antibody (Ab6tet) suggests that this approach could be used to enhance the activity of antibody-drug conjugates for which lysosomal delivery is required. By contrast, a high proportion of the bispecific, TAb6, persists on the plasma membrane where it is exposed for recognition by FcγRs and/or complement receptors, allowing antibody dependent cell-mediated cytotoxicity/phagocytosis (ADCC/ADCP) or complement-mediated cytotoxicity by appropriate effector cells.

Earlier studies have demonstrated that dual targeting of HER2 and HER3, using either bispecific scFvs or mixtures of individual antibodies specific for HER2 and HER3, reduces tumor cell growth in the presence of lapatinib. Significantly, here it was demonstrated that TAb6 is more effective than mixtures of trastuzumab and Ab6. This is consistent with the concept that TAb6 anchors HER3 into lapatinib-inactivated HER2-HER3 dimers, thereby sequestering it from interactions with other kinase competent partners and enabling Ab6 to bind to HER3 with increased avidity. By analogy with the observations of the inventors, the use of a bispecific scFv-human albumin fusion (MM-111) has been shown to have anti-tumor effects in the presence of heregulin, which were increased by the addition of lapatinib (McDonagh C F, Huhalov A, Harms B D, Adams S, Paragas V, Oyama S, et al. Antitumor activity of a novel bispecific antibody that targets the ErbB2/ErbB3 oncogenic unit and inhibits heregulin-induced activation of ErbB3. *Mol Cancer Ther* 2012; 11:582-93), although the efficacy of MM-111 was not directly compared with that of the anti-HER3 antibody, Ab6 (also called MM-121). Further, and by contrast with this earlier report, we observe lower levels of heregulin-induced proliferation and, for most conditions or cell lines, no significant anti-proliferative effects of monotherapy with lapatinib or trastuzumab in the presence of heregulin. These apparent discrepancies may be due to differences in assay conditions, such as the addition of heregulin following antibody treatment rather than simultaneous addition. An important difference between the activity of TAb6 and MM-111 is that, in the absence of heregulin and lapatinib, MM-111 does not induce proliferation. The design of TAb6 and MM-111 differs in several respects: first, the scFvs specific for HER2 and HER3 in MM-111 are distinct from those in TAb6. Although both the anti-HER3 scFv (H3) and Ab6 compete with heregulin for binding to HER3, this does not exclude the possibility that the two antibodies recognize distinct epitopes. The HER2-specific scFv, B1D2, binds to an epitope that does not overlap with trastuzumab. Second, TAb6 has two anti-HER2 and two anti-HER3 Fabs/Fvs per molecule, whereas MM-111 has one scFv of each specificity. Tetravalency is expected to enhance the avidity of the interaction with HER2/HER3. Third, TAb6 has an antibody Fc region whereas the scFvs in MM-111 are linked to albumin, resulting in variations in the 'span' distance of the Fv components of the two constructs. One or more of these factors could contribute to the different activities of MM-111 compared with TAb6. Significantly, the presence of an Fc region in TAb6 confers effector function activities such as ADCC. The surface retention of targeting antibodies such as TAb6 is expected to enhance ADCC and other cell-mediated cytotoxicity pathways, which in turn could enhance anti-tumor activity.

Collectively, the inventors have compared the effects of targeting HER2, HER3 or both receptors with several different antibody formats on the proliferation and signaling of breast cancer cell lines. These studies demonstrate that in the presence of the TKI inhibitor, lapatinib, a bispecific anti-HER2/HER3 antibody has higher activity than individual (multivalent) antibodies specific for HER2 and HER3 in inhibiting heregulin-induced signaling through the PI3K/Akt pathway and cell proliferation. These observations suggest that the use of such bispecifics in combination therapy with lapatinib to sequester HER3 into inactive heterodimers may provide an effective pathway for the treatment of cancer.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the illustrative embodiments of the present invention are not intended to be limited to the particular embodiments disclosed. Rather, they include all modifications and alternatives falling within the scope of the disclosure. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The invention claimed is:

1. A bispecific antibody comprising: an anti-HER2 antibody comprising two heavy chains and two light chains and an anti-HER3 single chain antibody variable fragment (Fv) comprising a heavy chain variable domain and a light chain variable domain, wherein said Fv is linked to each of the two CH3 domains of the anti-HER2 antibody, wherein the light chain variable domain of the anti-HER3 single chain Fv comprises amino acid residues 607-717 of SEQ ID NO: 1 and the heavy chain variable domain of the anti-HER3 single chain Fv comprises amino acid residues 473-591 of SEQ ID NO: 1, wherein the light chain variable domain of the anti-HER2 antibody comprises amino acid residues 20-127 of SEQ ID NO: 2 and the heavy chain variable domain of the anti-HER2 antibody comprises amino acid residues 20-139 of SEQ ID NO: 1, and wherein the bispecific antibody facilitates formation of HER2-HER3 heterodimers and inhibits the growth or proliferation of a cancer cell when administered or applied at a therapeutically effective amount and in combination with a tyrosine kinase inhibitor.

2. The bispecific antibody of claim 1, wherein the heavy chain of the anti-HER2 antibody is linked to a N' terminus end of the single chain Fv.

3. The bispecific antibody of claim 1, wherein the single chain Fv is linked to the CH3 domain by a linker comprising a Gly-Ser-Ser sequence.

4. The bispecific antibody of claim 1, wherein the single chain Fv comprises a $(Gly_4Ser)_n$ linker peptide between the heavy chain variable domain and the light chain variable domain.

5. The bispecific antibody of claim 1, wherein the cancer cell is a SK-BR-3 cell or BT-474 cell or HCC1419 cell or other breast cancer cell, and the proliferation of the cancer cell is reduced by at least 25% relative to a control cell.

6. The bispecific antibody of claim 1, wherein the bispecific antibody comprises a human antibody, a humanized antibody, or a chimeric antibody.

7. A composition comprising the bispecific antibody of claim 1 in a pharmaceutically acceptable carrier.

8. A method of treating a cancer in a subject comprising administering to the subject a therapeutically effective amount of the composition of claim 7 in combination with lapatinib or erlotinib to inhibit growth or proliferation of cancerous cells, wherein the subject is human and the cancerous cells express HER2 and HER3.

9. A method of treating a cancer in a subject comprising administering to the subject a therapeutically effective amount of a first agent comprising the bispecific antibody of claim 1 in combination with a therapeutically effective amount of a tyrosine kinase inhibitor, wherein the subject is human and the cancer expresses HER2 and HER3.

10. The method of claim 9, wherein the tyrosine kinase inhibitor is lapatinib or erlotinib.

11. The method of claim 9, wherein the tyrosine kinase inhibitor is selected from the group comprising a small molecule targeting IGF1R, a small molecule targeting EGFR, a small molecule targeting ErbB2, a small molecule targeting cMET, an mTOR inhibitor, and an MEK inhibitor.

12. The method of claim 8, wherein the composition and lapatinib or erlotinib are administered simultaneously.

* * * * *

SEQUENCE LISTING

<160> NUMBER OF SEQ ID NOS: 11

<210> SEQ ID NO 1
<211> LENGTH: 717
<212> TYPE: PRT
<213> ORGANISM: Artificial Sequence
<220> FEATURE:
<223> OTHER INFORMATION: Synthetic polypeptide

<400> SEQUENCE: 1

```
Met Gly Trp Ser Cys Ile Ile Leu Phe Leu Val Ala Thr Ala Thr Gly
 1               5                  10                  15

Val His Ser Gln Val Gln Leu Gln Glu Ser Gly Gly Gly Leu Val Gln
             20                  25                  30

Pro Gly Gly Ser Leu Arg Leu Ser Cys Ala Ala Ser Gly Phe Asn Ile
         35                  40                  45

Lys Asp Thr Tyr Ile His Trp Val Arg Gln Ala Pro Gly Lys Gly Leu
 50                  55                  60

Glu Trp Val Ala Arg Ile Tyr Pro Thr Asn Gly Tyr Thr Arg Tyr Ala
 65                  70                  75                  80

Asp Ser Val Lys Gly Arg Phe Thr Ile Ser Ala Asp Thr Ser Lys Asn
                 85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
```

```
            355                 360                 365
Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys Gly Ser Ser Gln Val Gln Leu Leu Glu Ser Gly
465                 470                 475                 480

Gly Gly Leu Val Gln Pro Gly Gly Ser Leu Arg Leu Ser Cys Ala Ala
                485                 490                 495

Ser Gly Phe Thr Phe Ser His Tyr Val Met Ala Trp Val Arg Gln Ala
            500                 505                 510

Pro Gly Lys Gly Leu Glu Trp Val Ser Ser Ile Ser Ser Ser Gly Gly
        515                 520                 525

Trp Thr Leu Tyr Ala Asp Ser Val Lys Gly Arg Phe Thr Ile Ser Arg
    530                 535                 540

Asp Asn Ser Lys Asn Thr Leu Tyr Leu Gln Met Asn Ser Leu Arg Ala
545                 550                 555                 560

Glu Asp Thr Ala Val Tyr Tyr Cys Thr Arg Gly Leu Lys Met Ala Thr
                565                 570                 575

Ile Phe Asp Tyr Trp Gly Gln Gly Thr Leu Val Thr Val Ser Ser Gly
            580                 585                 590

Gly Gly Gly Ser Gly Gly Gly Gly Ser Gly Gly Gly Gly Ser Asp Ile
        595                 600                 605

Gln Leu Thr Gln Pro Ala Ser Val Ser Gly Ser Pro Gly Gln Ser Ile
    610                 615                 620

Thr Ile Ser Cys Thr Gly Thr Ser Ser Asp Val Gly Ser Tyr Asn Val
625                 630                 635                 640

Val Ser Trp Tyr Gln Gln His Pro Gly Lys Ala Pro Lys Leu Ile Ile
                645                 650                 655

Tyr Glu Val Ser Gln Arg Pro Ser Gly Val Ser Asn Arg Phe Ser Gly
            660                 665                 670

Ser Lys Ser Gly Asn Thr Ala Ser Leu Thr Ile Ser Gly Leu Gln Thr
        675                 680                 685

Glu Asp Glu Ala Asp Tyr Tyr Cys Cys Ser Tyr Ala Gly Ser Ser Ile
    690                 695                 700

Phe Val Ile Phe Gly Gly Gly Thr Lys Val Thr Val Leu
705                 710                 715

<210> SEQ ID NO 2
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 2

Met Gly Trp Ser Cys Ile Ile Leu Phe Leu Val Ala Thr Ala Thr Gly
```

```
1               5                   10                  15
Val His Ser Asp Ile Glu Leu Thr Gln Ser Pro Ser Ser Leu Ser Ala
                20                  25                  30
Ser Val Gly Asp Arg Val Thr Ile Thr Cys Arg Ala Ser Gln Asp Val
                35                  40                  45
Asn Thr Ala Val Ala Trp Tyr Gln Gln Lys Pro Gly Lys Ala Pro Lys
 50                  55                  60
Leu Leu Ile Tyr Ser Ala Ser Phe Leu Tyr Ser Gly Val Pro Ser Arg
65                   70                  75                  80
Phe Ser Gly Ser Arg Ser Gly Thr Asp Phe Thr Leu Thr Ile Ser Ser
                85                  90                  95
Leu Gln Pro Glu Asp Phe Ala Thr Tyr Tyr Cys Gln Gln His Tyr Thr
                100                 105                 110
Thr Pro Pro Thr Phe Gly Gln Gly Thr Lys Leu Glu Ile Lys Arg Thr
                115                 120                 125
Val Ala Ala Pro Ser Val Phe Ile Phe Pro Pro Ser Asp Glu Gln Leu
 130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
                180                 185                 190
Ser Leu Ser Ser Thr Leu Thr Leu Ser Lys Ala Asp Tyr Glu Lys His
                195                 200                 205
Lys Val Tyr Ala Cys Glu Val Thr His Gln Gly Leu Ser Ser Pro Val
 210                 215                 220
Thr Lys Ser Phe Asn Arg Gly Glu Cys
225                 230
```

<210> SEQ ID NO 3
<211> LENGTH: 716
<212> TYPE: PRT
<213> ORGANISM: Artificial Sequence
<220> FEATURE:
<223> OTHER INFORMATION: Synthetic polypeptide

<400> SEQUENCE: 3

```
Met Gly Trp Ser Cys Ile Ile Leu Phe Leu Val Ala Thr Ala Thr Gly
1               5                   10                  15
Val His Ser Gln Val Gln Leu Gln Glu Ser Gly Gly Gly Leu Val Gln
                20                  25                  30
Pro Gly Gly Ser Leu Arg Leu Ser Cys Ala Ala Ser Gly Phe Thr Phe
                35                  40                  45
Ser His Tyr Val Met Ala Trp Val Arg Gln Ala Pro Gly Lys Gly Leu
 50                  55                  60
Glu Trp Val Ser Ser Ile Ser Ser Gly Gly Trp Thr Leu Tyr Ala
65                   70                  75                  80
Asp Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
                100                 105                 110
Tyr Tyr Cys Thr Arg Gly Leu Lys Met Ala Thr Ile Phe Asp Tyr Trp
                115                 120                 125
Gly Gln Gly Thr Leu Val Thr Val Ser Ser Ala Ser Thr Lys Gly Pro
```

-continued

```
            130                 135                 140
Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Gln Thr Tyr Ile Cys Asn Val Asn
        210                 215                 220

His Lys Pro Ser Asn Thr Lys Val Asp Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
                275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Arg Asp Glu Leu Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
450                 455                 460

Ser Pro Gly Lys Gly Ser Gln Val Gln Leu Leu Glu Ser Gly Gly
465                 470                 475                 480

Gly Leu Val Gln Pro Gly Gly Ser Leu Arg Leu Ser Cys Ala Ala Ser
                485                 490                 495

Gly Phe Thr Phe Ser His Tyr Val Met Ala Trp Val Arg Gln Ala Pro
                500                 505                 510

Gly Lys Gly Leu Glu Trp Val Ser Ser Ile Ser Ser Ser Gly Gly Trp
                515                 520                 525

Thr Leu Tyr Ala Asp Ser Val Lys Gly Arg Phe Thr Ile Ser Arg Asp
        530                 535                 540

Asn Ser Lys Asn Thr Leu Tyr Leu Gln Met Asn Ser Leu Arg Ala Glu
545                 550                 555                 560
```

```
Asp Thr Ala Val Tyr Tyr Cys Thr Arg Gly Leu Lys Met Ala Thr Ile
                565                 570                 575

Phe Asp Tyr Trp Gly Gln Gly Thr Leu Val Thr Val Ser Ser Gly Gly
            580                 585                 590

Gly Gly Ser Gly Gly Gly Gly Ser Gly Gly Gly Gly Ser Asp Ile Gln
        595                 600                 605

Leu Thr Gln Pro Ala Ser Val Ser Gly Ser Pro Gly Gln Ser Ile Thr
    610                 615                 620

Ile Ser Cys Thr Gly Thr Ser Ser Asp Val Gly Ser Tyr Asn Val Val
625                 630                 635                 640

Ser Trp Tyr Gln Gln His Pro Gly Lys Ala Pro Lys Leu Ile Ile Tyr
                645                 650                 655

Glu Val Ser Gln Arg Pro Ser Gly Val Ser Asn Arg Phe Ser Gly Ser
            660                 665                 670

Lys Ser Gly Asn Thr Ala Ser Leu Thr Ile Ser Gly Leu Gln Thr Glu
        675                 680                 685

Asp Glu Ala Asp Tyr Tyr Cys Cys Ser Tyr Ala Gly Ser Ser Ile Phe
    690                 695                 700

Val Ile Phe Gly Gly Gly Thr Lys Val Thr Val Leu
705                 710                 715

<210> SEQ ID NO 4
<211> LENGTH: 237
<212> TYPE: PRT
<213> ORGANISM: Artificial Sequence
<220> FEATURE:
<223> OTHER INFORMATION: Synthetic polypeptide

<400> SEQUENCE: 4

Met Gly Trp Ser Cys Ile Ile Leu Phe Leu Val Ala Thr Ala Thr Gly
1               5                   10                  15

Val His Ser Asp Ile Glu Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Ser Tyr Asn Val Val Ser Trp Tyr Gln Gln His Pro Gly Lys Ala
    50                  55                  60

Pro Lys Leu Ile Ile Tyr Glu Val Ser Gln Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Thr Glu Asp Glu Ala Asp Tyr Tyr Cys Cys Ser Tyr
            100                 105                 110

Ala Gly Ser Ser Ile Phe Val Ile Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205
```

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235

<210> SEQ ID NO 5
<211> LENGTH: 2151
<212> TYPE: DNA
<213> ORGANISM: Artificial Sequence
<220> FEATURE:
<223> OTHER INFORMATION: Synthetic oligonucleotide

<400> SEQUENCE: 5

| | | | | |
|---|---|---|---|---|
| atgggatgga | gctgtatcat | cctcttcttg | gtagcaacag | ctacaggtgt | cccactcccag | 60 |
| gttcagctgc | aggagtctgg | cggtggcctg | gtgcagccag | ggggctcact | ccgtttgtcc | 120 |
| tgtgcagctt | ctggcttcaa | cattaaagac | acctatatac | actgggtgcg | tcaggccccg | 180 |
| ggtaagggcc | tggaatgggt | tgcaaggatt | tatcctacga | atggttatac | tagatatgcc | 240 |
| gatagcgtca | agggccgttt | cactataagc | gcagacacat | ccaaaaacac | agcctaccta | 300 |
| cagatgaaca | gcctgcgtgc | tgaggacact | gccgtctatt | attgttctag | atggggaggg | 360 |
| gacggcttct | atgctatgga | ctactgggt | caaggaaccc | tggtcaccgt | ctcctcggcc | 420 |
| tccaccaagg | gcccatcggt | cttccccctg | gcaccctcct | ccaagagcac | ctctgggggc | 480 |
| acagcggccc | tgggctgcct | ggtcaaggac | tacttccccg | aaccggtgac | ggtgtcgtgg | 540 |
| aactcaggcg | ccctgaccag | cggcgtgcac | accttcccgg | ctgtcctaca | gtcctcagga | 600 |
| ctctactccc | tcagcagcgt | ggtgaccgtg | ccctccagca | gcttgggcac | ccagacctac | 660 |
| atctgcaacg | tgaatcacaa | gcccagcaac | accaaggtgg | acaagaaagt | tgagcccaaa | 720 |
| tcttgtgaca | aaactcacac | atgcccaccg | tgcccagcac | ctgaactcct | gggggggaccg | 780 |
| tcagtcttcc | tcttcccccc | aaaacccaag | gacaccctca | tgatctcccg | gacccctgag | 840 |
| gtcacatgcg | tggtggtgga | cgtgagccac | gaagaccctg | aggtcaagtt | caactggtac | 900 |
| gtggacggcg | tggaggtgca | taatgccaag | acaaagccgc | gggaggagca | gtacaacagc | 960 |
| acgtaccgtg | tggtcagcgt | cctcaccgtc | ctgcaccagg | actggctgaa | tggcaaggag | 1020 |
| tacaagtgca | aggtctccaa | caaagccctc | ccagccccca | tcgagaaaac | catctccaaa | 1080 |
| gccaaagggc | agccccgaga | accacaggtg | tacaccctgc | ccccatcccg | ggatgagctg | 1140 |
| accaagaacc | aggtcagcct | gacctgcctg | gtcaaaggct | tctatcccag | cgacatcgcc | 1200 |
| gtggagtggg | agagcaatgg | gcagccggag | aacaactaca | agaccacgcc | tcccgtgctg | 1260 |
| gactccgacg | gctccttctt | cctctacagc | aagctcaccg | tggacaagag | caggtggcag | 1320 |
| caggggaacg | tcttctcatg | ctccgtgatg | catgaggctc | tgcacaacca | ctacacgcag | 1380 |
| aagagcctct | ccctgtctcc | gggtaaaggc | tcgagccagg | tgcagctgct | ggagagcggc | 1440 |
| ggagggctgg | tccagccagg | cggcagcctg | aggctgtcct | gcgccgccag | cggcttcacc | 1500 |
| ttcagccact | acgtgatggc | ctgggtgcgg | caggcccag | gcaagggcct | ggaatgggtg | 1560 |
| tccagcatca | gcagcagcgg | cggctggacc | ctgtacgccg | acagcgtgaa | gggcaggttc | 1620 |
| accatcagca | gggacaacag | caagaacacc | ctgtacttgc | agatgaacag | cctgagggcc | 1680 |
| gaggacaccg | ccgtgtacta | ctgcaccagg | ggcctgaaga | tggccaccat | cttcgactac | 1740 |
| tggggccagg | gcaccctggt | cacggtctcc | tcggggaggtg | gcggatctgg | tggaggtggc | 1800 |
| agtggtggag | gtggctcaga | catccagctc | acccagcccg | ccagcgtgag | cggcagccca | 1860 |

| ggccagagca tcaccatcag ctgcaccggc accagcagcg acgtgggcag ctacaacgtg | 1920 |
| gtgtcctggt atcagcagca ccccggcaag gcccccaagc tgatcatcta cgaggtgtcc | 1980 |
| cagaggccca gcggcgtgag caacaggttc agcggcagca agagcggcaa caccgccagc | 2040 |
| ctgaccatca gcggcttgca gaccgaggac gaggccgact actactgttg cagctacgcc | 2100 |
| ggcagcagca tcttcgtgat cttcggcgga gggaccaagg tgaccgtcct a | 2151 |

```
<210> SEQ ID NO 6
<211> LENGTH: 699
<212> TYPE: DNA
<213> ORGANISM: Artificial Sequence
<220> FEATURE:
<223> OTHER INFORMATION: Synthetic oligonucleotide

<400> SEQUENCE: 6
```

| atgggatgga gctgtatcat cctcttcttg gtagcaacag ctacaggtgt ccactccgac | 60 |
| atcgagctca cccagtcccc aagctccctg tccgcctctg tgggcgatag agtcaccatc | 120 |
| acctgccgtg ccagtcagga tgtgaatact gctgtagcct ggtatcaaca gaaaccagga | 180 |
| aaagctccga aactactgat ttactcggca tccttcctct actctggagt cccttctcgc | 240 |
| ttctctggat ccagatctgg gacggatttc actctaacca tcagcagtct acagccggaa | 300 |
| gacttcgcaa cttattactg tcagcaacat tatactactc ctcccacgtt cggacagggt | 360 |
| accaagctcg agatcaaacg aactgtggct gcaccatctg tcttcatctt cccgccatct | 420 |
| gatgagcagt tgaaatctgg aactgcctct gttgtgtgcc tgctgaataa cttctatccc | 480 |
| agagaggcca aagtacagtg gaaggtggat aacgccctcc aatcgggtaa ctcccaggag | 540 |
| agtgtcacag agcaggacag caaggacagc acctacagcc tcagcagcac cctgacgctg | 600 |
| agcaaagcag actacgagaa acacaaagtc tacgcctgcg aagtcaccca tcagggcctg | 660 |
| agctcgcccg tcacaaagag cttcaacagg ggagagtgt | 699 |

```
<210> SEQ ID NO 7
<211> LENGTH: 2151
<212> TYPE: DNA
<213> ORGANISM: Artificial Sequence
<220> FEATURE:
<223> OTHER INFORMATION: Synthetic oligonucleotide

<400> SEQUENCE: 7
```

| atgggatgga gctgtatcat cctcttcttg gtagcaacag ctacaggtgt ccactcccag | 60 |
| gtccaactgc aggagagcgg cggagggctg gtccagccag cggcagcct gaggctgtcc | 120 |
| tgcgccgcca gcggcttcac cttcagccac tacgtgatgg cctgggtgcg gcaggcccca | 180 |
| ggcaagggcc tggaatgggt gtccagcatc agcagcagcg gcggctggac cctgtacgcc | 240 |
| gacagcgtga agggcaggtt caccatcagc agggacaaca gcaagaacac cctgtacttg | 300 |
| cagatgaaca gcctgagggc cgaggacacc gccgtgtact actgcaccag ggccctgaag | 360 |
| atggccacca tcttcgacta ctggggccag ggcaccctgg tcaccgtctc ctcagcctcc | 420 |
| accaagggcc catcggtctt ccccctggca ccctcctcca agagcacctc tgggggcaca | 480 |
| gcggccctgg gctgcctggt caaggactac ttccccgaac cggtgacggt gtcgtggaac | 540 |
| tcaggcgccc tgaccagcgg cgtgcacacc ttcccggctg tcctacagtc ctcaggactc | 600 |
| tactccctca gcagcgtggt gactgtgccc tccagcagct tgggcaccca gacctacatc | 660 |
| tgcaacgtga atcacaagcc cagcaacacc aaggtggaca agaaagttga gcccaaatct | 720 |
| tgtgacaaaa ctcacacatg cccaccgtgc ccagcacctg aactcctggg gggaccgtca | 780 |

-continued

```
gtcttcctct tccccccaaa acccaaggac accctcatga tctcccggac ccctgaggtc      840
acatgcgtgg tggtggacgt gagccacgaa gaccctgagg tcaagttcaa ctggtacgtg      900
gacggcgtgg aggtgcataa tgccaagaca aagccgcggg aggagcagta acagcacg        960
taccgtgtgg tcagcgtcct caccgtcctg caccaggact ggctgaatgg caaggagtac     1020
aagtgcaagg tctccaacaa agccctccca gcccccatcg agaaaaccat ctccaaagcc     1080
aaagggcagc ccgagaacc acaggtgtac accctgcccc catcccggga tgagctgacc      1140
aagaaccagg tcagcctgac ctgcctggtc aaaggcttct atcccagcga catcgccgtg     1200
gagtgggaga gcaatgggca gccggagaac aactacaaga ccacgcctcc cgtgctggac     1260
tccgacggct ccttcttcct ctacagcaag ctcaccgtgg acaagagcag gtggcagcag     1320
gggaacgtct tctcatgctc cgtgatgcat gaggctctgc acaaccacta cacgcagaag     1380
agcctctccc tgtctccggg taaaggctcg agccaggtgc agctgctgga gagcggcgga     1440
gggctggtcc agccaggcgg cagcctgagg ctgtcctgcg ccgccagcgg cttcaccttc     1500
agccactacg tgatggcctg ggtgcggcag gccccaggca agggcctgga atgggtgtcc     1560
agcatcagca gcagcggcgg ctggaccctg tacgccgaca gcgtgaaggg caggttcacc     1620
atcagcaggg acaacagcaa gaacaccctg tacttgcaga tgaacagcct gagggccgag     1680
gacaccgccg tgtactactg caccagggc ctgaagatgg ccaccatctt cgactactgg      1740
ggccagggca ccctggtcac ggtctcctcg ggaggtggcg gatctggtgg aggtggcagt     1800
ggtggaggtg gctcagacat ccagctcacc cagcccgcca gcgtgagcgg cagcccaggc     1860
cagagcatca ccatcagctg caccggcacc agcagcgacg tgggcagcta caacgtggtg     1920
tcctggtatc agcagcaccc cggcaaggcc cccaagctga tcatctacga ggtgtcccag     1980
aggcccagcg gcgtgagcaa caggttcagc ggcagcaaga gcggcaacac cgccagcctg     2040
accatcagcg gcttgcagac cgaggacgag gccgactact actgttgcag ctacgccggc     2100
agcagcatct tcgtgatctt cggcggaggg accaaggtga ccgtcctata a              2151
```

<210> SEQ ID NO 8
<211> LENGTH: 714
<212> TYPE: DNA
<213> ORGANISM: Artificial Sequence
<220> FEATURE:
<223> OTHER INFORMATION: Synthetic oligonucleotide

<400> SEQUENCE: 8

```
atgggatgga gctgtatcat cctcttcttg gtagcaacag ctacaggtgt ccactccgac       60
atcgagctca cccagcccgc cagcgtgagc ggcagcccag gccagagcat caccatcagc      120
tgcaccggca ccagcagcga cgtgggcagc tacaacgtgg tgtcctggta tcagcagcac      180
cccggcaagg cccccaagct gatcatctac gaggtgtccc agaggcccag cggcgtgagc      240
aacaggttca gcggcagcaa gagcggcaac accgccagcc tgaccatcag cggcttgcag      300
accgaggacg aggccgacta ctactgttgc agctacgccg gcagcagcat cttcgtgatc      360
ttcggcggag gaccaagct cgagatcaaa cgaactgtgg ctgcaccatc tgtcttcatc      420
ttcccgccat ctgatgagca gttgaaatct ggaactgcct ctgttgtgtg cctgctgaat      480
aacttctatc ccagagaggc caaagtacag tggaaggtgg ataacgccct ccaatcgggt      540
aactcccagg agagtgtcac agagcaggac agcaaggaca gcacctacag cctcagcagc      600
accctgacgc tgagcaaagc agactacgag aaacacaaag tctacgcctg cgaagtcacc      660
```

```
catcagggcc tgagttcgcc cgtcacaaag agcttcaaca ggggagagtg ttaa            714
```

```
<210> SEQ ID NO 9
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 9

Met Gly Trp Ser Cys Ile Ile Leu Phe Leu Val Ala Thr Ala Thr Gly
1               5                   10                  15

Val His Ser

<210> SEQ ID NO 10
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 11

Gly Gly Gly Ser
1
```